(12) United States Patent
Peng et al.

(10) Patent No.: US 11,944,615 B2
(45) Date of Patent: Apr. 2, 2024

(54) COMBINATION THERAPY FOR TREATMENT OF LKB1 DEFICIENT CANCERS

(71) Applicant: New York University, New York, NY (US)

(72) Inventors: David Peng, Mohegan Lake, NY (US); Kwok-Kin Wong, Arlington, MA (US); Jiehui Deng, Port Washington, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 17/466,776

(22) Filed: Sep. 3, 2021

(65) Prior Publication Data

US 2022/0062260 A1  Mar. 3, 2022

Related U.S. Application Data

(60) Provisional application No. 63/074,147, filed on Sep. 3, 2020.

(51) Int. Cl.
| | | |
|---|---|---|
| *A61K 31/4545* | (2006.01) | |
| *A61K 31/497* | (2006.01) | |
| *A61K 31/505* | (2006.01) | |
| *A61K 45/06* | (2006.01) | |
| *A61P 35/00* | (2006.01) | |

(52) U.S. Cl.
CPC ........ *A61K 31/4545* (2013.01); *A61K 31/497* (2013.01); *A61K 31/505* (2013.01); *A61K 45/06* (2013.01); *A61P 35/00* (2018.01)

(58) Field of Classification Search
CPC .............................. A61K 31/519; A61P 35/00
See application file for complete search history.

(56) References Cited

U.S. PATENT DOCUMENTS

2021/0093597 A1* 4/2021 Deng .................... A61K 45/06

FOREIGN PATENT DOCUMENTS

| WO | WO-2017117196 A1 * | 7/2017 | ......... A61K 31/4406 |
|---|---|---|---|
| WO | WO-2020150480 A1 * | 7/2020 | |

OTHER PUBLICATIONS

Whang (Oncogene pp. 1-11, published 2015) (Year: 2015).*

* cited by examiner

*Primary Examiner* — Theodore R. Howell
*Assistant Examiner* — George W Kosturko
(74) *Attorney, Agent, or Firm* — Hodgson Russ LLP

(57) ABSTRACT

Provided are methods of sensitizing LKB1/STK11 deficient cancers to immune therapy. A method for treatment for LKB1/STK11 deficient cancers is provided comprising administration of inhibitor or inhibitors of one or more of NAMPT, CD38, SHP2, CXCR1/2, HDAC4 and PARP in combination with immunotherapy.

13 Claims, 14 Drawing Sheets

Specification includes a Sequence Listing.

A.

B.

A.

B.

A.

B.

COMBINATION THERAPY FOR TREATMENT OF LKB1 DEFICIENT CANCERS

CROSS-REFERENCE TO RELATED APPLICATIONS

This application claims priority to U.S. Provisional application no. 63/074,147, filed on Sep. 3, 2020, the disclosure of which is incorporated herein by reference.

INCORPORATION BY REFERENCE OF SEQUENCE LISTING

The present application is being filed with a Sequence Listing in electronic format. The Sequence Listing is provided as an ASCII text file titled 058636_00383_Seq_listing_ST25.txt created on Sep. 2, 2021 and is 33,572 bytes in size. The information in electronic format of the Sequence Listing is incorporated herein by reference in its entirety.

BACKGROUND OF THE DISCLOSURE

Lung cancer is the leading cause of cancer-associated deaths worldwide because of resistance to conventional therapies and recurrent disease. A main hallmark of lung cancer is the ability to evade immune destruction due, in part, to upregulation of the immune checkpoint ligand PD-L1, which activates the PD-1 receptor on lymphocytes to suppress cytotoxic activity. Accordingly, therapeutic blockade of PD-1 or PD-L1 (PD-(L)1) has significantly improved overall lung cancer patient survival. Despite the early success of immunotherapies, a vast majority of lung cancer patients (>80%) do not show durable response to immune checkpoint blockade, suggesting innate or acquired drug resistance. Thus, understanding the mechanisms governing immune checkpoint blockade resistance is critical in improving lung cancer patient survival.

KRAS mutations occur in approximately 30% of patients with lung adenocarcinomas and correlate with poorer overall survival. The lack of specific inhibitors against the multitude of KRAS mutations renders treatment difficult, but presents immunotherapy as a promising alternative to targeted therapies. Nonetheless, loss-of-function mutations in tumor suppressors such as TP53 (KP) and STK1/LKB1 (KL) frequently co-occur with KRAS mutations and confer differential sensitivities to PD-(L)1 blockade. Although KP and KL tumors possess an immunosuppressive microenvironment, the mechanisms of immune evasion differ between the two tumor subtypes. While KP tumors express high levels of PD-L1 and are responsive to anti-PD-(L)1 therapies, KL tumors have low expression of PD-L1 and are resistant to immune checkpoint blockade. However, as a consequence of LKB1 pleiotropy, immune evasion and drug resistance mechanisms due to LKB1 loss remain poorly defined, and as a result, options for treatment of LKB1 deficient tumors are limited.

SUMMARY OF THE DISCLOSURE

The present disclosure describes that while LKB1 deficient cancer cells do not respond well to either targeted therapy or immune therapy, exposure to inhibitors of Nicotinamide Phosphoribosyltransferase (NAMPT), CD38, Histone Deacetylase 4 (HDAC4), poly adenosine diphosphate-ribose polymerase (PARP), SH2 containing protein tyrosine phosphatase-2 (SHP2) or CXC Receptor 1 or 2 (CXCR1/2) sensitizes such cells to immune therapy. As such, this disclosure provides a method for treatment of cancer, wherein the cancer cells are LKB1 deficient by sensitizing the cells to immune therapy and then administering the immune therapy.

In an aspect this disclosure provides a method of treatment of LKB1 deficient cancers (e.g., tumors) comprising administering to an individual in need of treatment, one or more inhibitors of one or more of NAMPT, CD38, HDAC4, PARP, SHP2 and CXCR1/2, in combination with immune based therapy. The tumor cells may optionally also have a KRAS mutation. In an embodiment, the cancer is lung cancer.

In an embodiment, this disclosure provides a method of treatment of LKB1 deficient cancers (e.g., tumors), wherein the cancer cells are LKB1 deficient, and optionally also have KRAS mutation, comprising administering to an individual in need of treatment, one or more inhibitors of one or more of NAMPT, CD38, HDAC4, PARP, SHP2 and CXCR1/2, determining that immune checkpoints are upregulated, and administering immune based therapy. In an embodiment, the cancer is lung cancer.

DESCRIPTION OF THE DISCLOSURE

Figure 1:
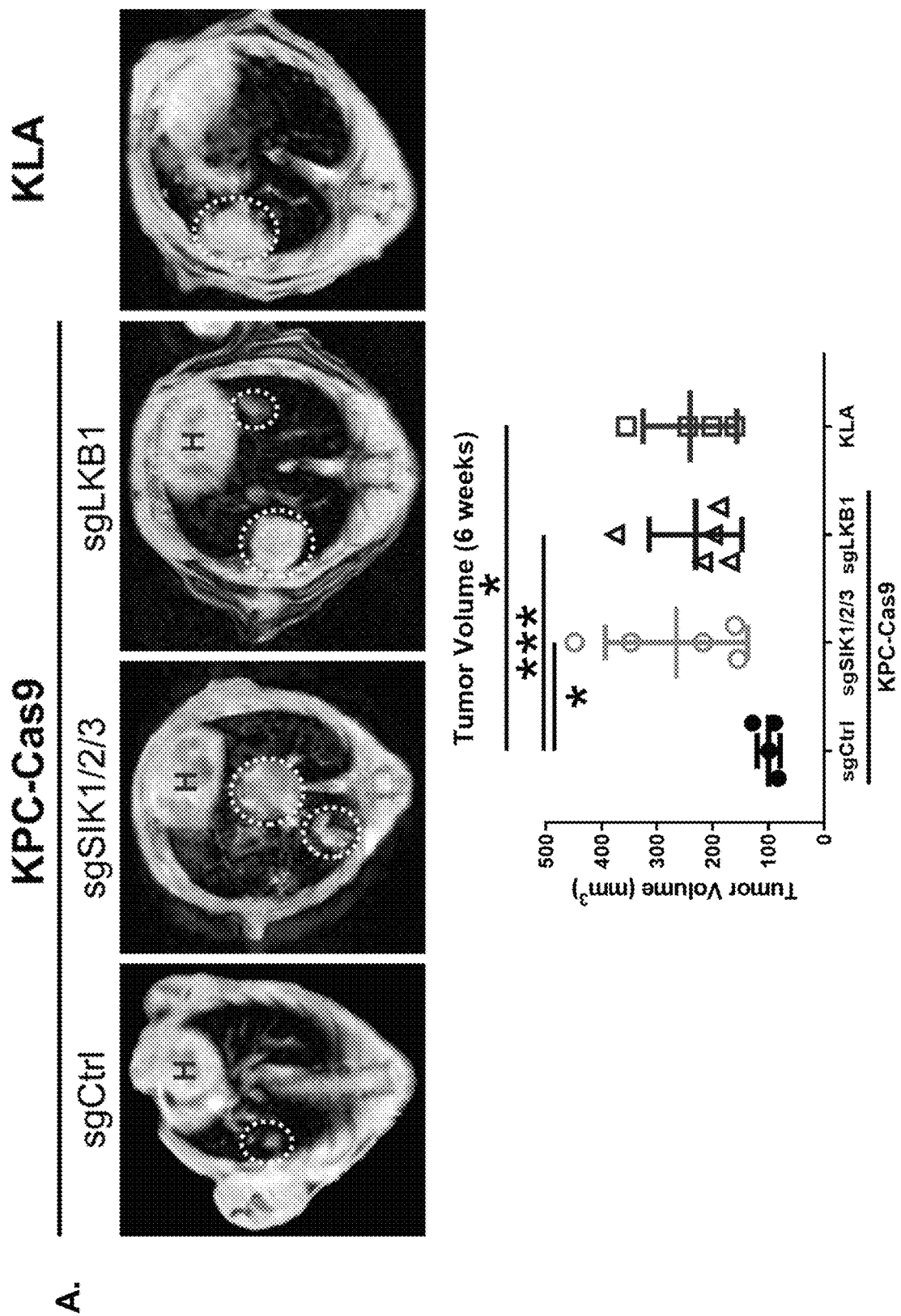
FIG. 1. Loss of SIK and LKB1 promotes tumor growth and decreases tumor infiltrating antigen presenting myeloid cells. A) Top: Representative MM images of mice lungs transplanted with KP cell line tumor allografts (KPC) with SIK or LKB1 knockout or KL cell line tumor allografts (KLA). Bottom: Quantification of total lung tumor volume in indicated tumor allografts. B) Percent of indicated immune populations as assess by flow cytometry relative to $CD^{45+}$ cells or parental populations in lung tumor tissues. "H" indicates the heart. Dotted circles represent tumors. $*P<0.05$, $P<0.01$, $*P<0.001$.
Figure 1:
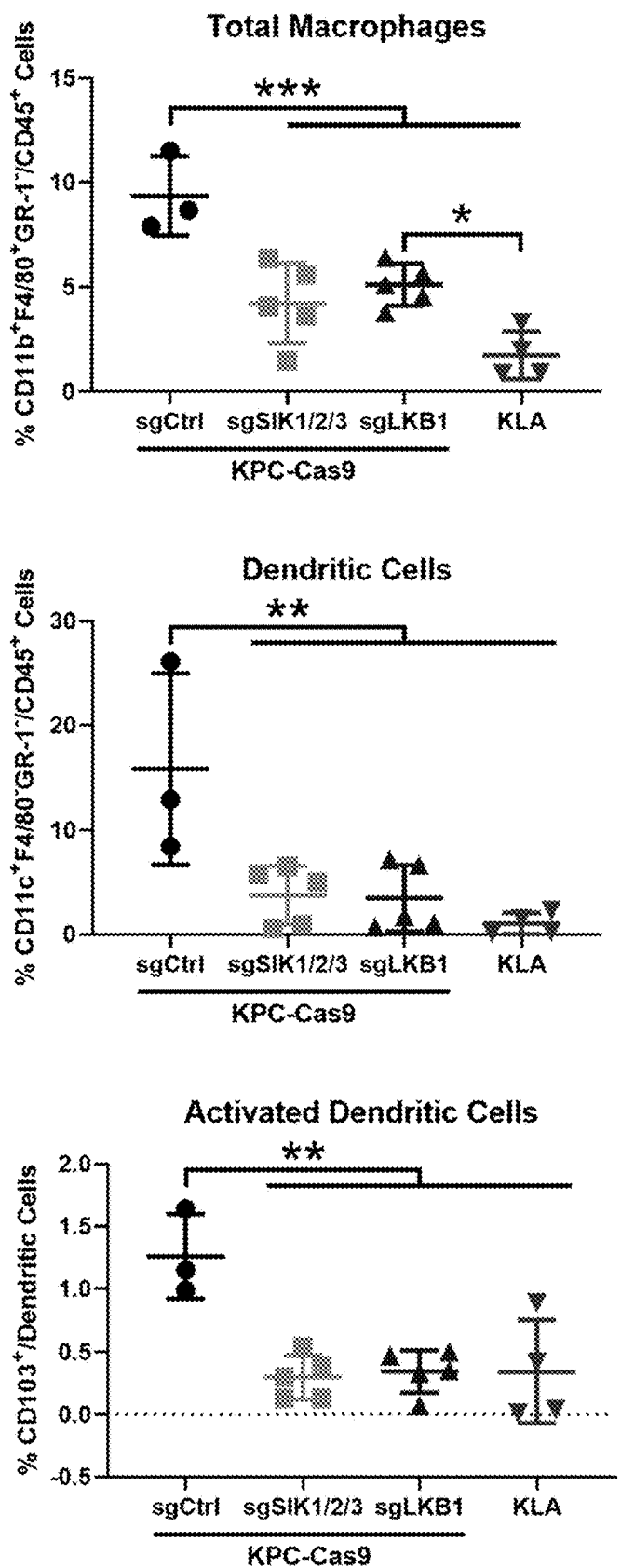

The present disclosure provides compositions and methods for treatment of cancers characterized by LKB1/STK11 mutations. In the present study, it was identified that inhibition of NAMPT, CD38, HDAC4, SHP2, CXCR1/2 or PARP sensitizes tumors to immune therapy. The present disclosure provides a method for treatment of LKB1/STK11 deficient cancers comprising administration of inhibitor or inhibitors of NAMPT, CD38, SHP2, CXCR1/2, HDAC4 and/or PARP in combination with immunotherapy. The present disclosure also provides compositions and kits for the treatment of LKB1/STK11 deficient cancers.

Throughout this application, the use of the singular form encompasses the plural form and vice versa. For example, "a", or "an" also includes a plurality of the referenced items, unless otherwise indicated.

Where a range of values is provided in this disclosure, it should be understood that each intervening value, and all intervening ranges, between the upper and lower limit of that range is also included, unless clearly indicated otherwise. The upper and lower limits from within the broad range may independently be included in the smaller ranges encompassed within the disclosure.

The term "therapeutically effective amount" as used herein refers to an amount of an agent sufficient to achieve, in a single or multiple doses, the intended purpose of treatment. Treatment does not have to lead to complete cure, although it may. Treatment can mean alleviation of one or more of the symptoms or markers of the indication. The exact amount desired or required will vary depending on the particular compound or composition used, its mode of administration, patient specifics and the like. Appropriate effective amount can be determined by one of ordinary skill in the art informed by the instant disclosure using only routine experimentation. Within the meaning of the disclosure, "treatment" also includes prophylaxis and treatment of relapse, as well as the alleviation of acute or chronic signs, symptoms and/or malfunctions associated with the indication. Treatment can be orientated symptomatically, for example, to suppress symptoms. It can be effected over a short period, over a medium term, or can be a long-term treatment, such as, for example within the context of a maintenance therapy. Administrations may be intermittent, periodic, or continuous.

The terms "LKB1 mutant", "LKB1 deficient" are used interchangeably with LKB1/STK11 deficient or mutant, STK11 deficient and STK11 mutant. All refer to a loss of function mutation in the gene, or a defect in the function of the protein. The nucleotide sequence of human LKB1 (also referred to as STK11) is available under Accession No. NB007460 (SEQ ID NO:1), and the amino acid sequence of the human protein STK11 is available under Accession No. NP 000446 (SEQ ID NO:2) from GenBank. All nucleotide sequences described herein, their RNA and DNA equivalents, and complimentary sequences are included in this disclosure. All polynucleotide and amino acid sequences associated with GenBank accession numbers (or other similar databases) described in this disclosure are incorporated herein by reference as those sequences are listed in the database as of the priority filing date of this application or patent.

LKB1 deficient cells may be identified by detecting at the nucleic acid level or at the protein level. The loss of function may be due to nucleic acid that is translated or transcribed at a detectably lower level in a cancer cell, in comparison to a normal cell. The loss of function may be due to gene deletion, mutation of a gene rendering the gene non-functional with respect to transcription or translation, transcription, post transcriptional processing, translation, post-translational processing, cellular localization (e.g., organelle, cytoplasm, nucleus, cell surface), or RNA and protein stability, as compared to a control, or a protein with significantly less activity compared to a control. Loss of function may be manifested as underexpression and can be detected using conventional techniques for detecting mRNA (i.e., RT-PCR, PCR, hybridization) or proteins (i.e., ELISA, immunoblotting, immunohistochemical techniques). Underexpression can be 5%, 10%, 20%, 30%, 40%, 50%, 60%, 70%, 80%, 90% or less in comparison to a control.

The present disclosure is based on the unexpected identification that the dysregulation of $NAD^+$ synthesis and catalysis, which promotes a suppressive tumor immune environment in LKB1 cancers, is mediated by one or more of NAMPT, CD38, HDAC4, SHP2, CXCR1/2 and PARP. We demonstrate that the $NAD^+$ synthesis gene NAMPT and the $NAD^+$ consuming enzymes CD38 and HDAC4 are upregulated in mutant KRAS;LKB1 lung cancers. Dysregulated tumor $NAD^+$ levels promotes an immune suppressive microenvironment while epigenetically suppressing PD-L1 expression in KL lung tumors, promoting immune evasion and resistance to immune checkpoint blockade therapies. Moreover, SHP2 inhibition and CXCR1/2 blockade can sensitize KL tumors through suppressing gMDSC and activate effector T cells. Based at least on these observations, the present method provides a method where one or more of NAMPT, CD38, HDAC4, PARP, SHP2 and/or CXCR1/2 inhibitors can be used to sensitize cancer cells, particularly LKB1 deficient cancel cells, to immune therapy.

In an aspect, this disclosure provides a method for sensitizing LKB1 deficient cancer cells to immune therapy by exposure of the cells to an inhibitor or inhibitors of one or more of NAMPT, CD38, HDAC4, PARP, SHP2 and CXCR1/2. The cancer cells may also be deficient in KRAS. Thus, in an embodiment, cancer cells may be sensitized to immune therapy by contacting the cells with an effective amount of an inhibitor or inhibitors of one or more of NAMPT, CD38, HDAC4, PARP, SHP2 and CXCR1/2.

Cancer cells may be tested for the presence of LKB1 deficiency such as a loss-of-function mutation and for KRAS mutation, such as constitutively activated KRAS mutation. The loss-of-function testing can be carried out on any biological sample, including sections of tissues such as biopsy samples and frozen sections prepared from tissues taken for histologic purposes. Samples may include tumor tissue samples, blood and blood fractions (e.g., serum, platelets, red blood cells, and the like), sputum, bronchoalveolar lavage, cultured cells, e.g., primary cultures, explants, and transformed cells, stool, urine, and the like. A biological sample is typically obtained from a mammal, such as a human, but may be obtained from a farm animal or a domesticated animal. A biopsy may be obtained by standard techniques including, excisional biopsy, incisional biopsy, needle biopsy, surgical biopsy, and bone marrow biopsy. Biopsy techniques are described in in Harrison's Principles of Internal Medicine, Kasper, et al., eds., 16th ed., 2005).

In an embodiment, this disclosure provides a method for treating LKB1 deficient cancers (e.g., tumors or blood cancers in which KRAS mutant/LKB1 deficient cells are present) in an individual by administration to the individual of a therapeutically effective amount of inhibitor or inhibitors of one or more of NAMPT, CD38, HDAC4, PARP, SHP2 and CXCR1/2, in combination with immune therapy. In an embodiment, the LKB1 deficient cancer cells may also carry a KRAS mutation (e.g., constitutively activated KRAS mutation). For example, the cancer cells may carry one or more KRAS mutation and one or more loss-of-function mutations in LKB1. The KRAS mutation may be constitutively active mutation.

In an embodiment, the disclosure provides a method of treating LKB1 deficient cancers in an individual by administration to the individual of a therapeutically effect amount of inhibitor or inhibitors of one or more of NAMPT, CD38, HDAC4, PARP, SHP2 and CXCR1/2, without immune therapy.

Examples of PARP inhibitors (PARPi) useful for the present methods include, but are not limited to, NU1025; 3-aminobenzamide; 4-amino-1,8-naphthalimide; 1,5-isoquinolinediol; 6(5H)-phenanthriddinone; 1,3,4,5,-tetrahydrobenzo(c)(1,6)-and (c)(1,7)-naphthyridin-6 ones; adenosine substituted 2,3-dihydro-1H-isoindol-1-ones; AG14361; AG014699; 2-(4-chlorophenyl)-5-quinoxalinecarboxamide; 5-chloro-2-[3-(4-phenyl-3,6-dihydro-1(2H)-pyridinyl)propyl]-4(3H)-quinazolinone; isoindolinone derivative INO-1001; 4-hydroxyquinazoline; 2-[3-[4-(4-chlorophenyl)1-piperazinyl]propyl]-4-3(4)-quinazolinone; 1,5-dihydroxyisoquinoline (DHIQ); 3,4-dihydro-5 [4-(1-piperidinyl)(butoxy)-1(2H)-isoquinolone; CEP-6800; GB-15427; PJ34; DPQ; BS-201; AZD2281 (Olaparib); BS401; CHP101; CHP102; INH2BP; BSI201; BSI401; TIQ-A; an imidazobenzodiazepine; 8-hydroxy-2-methylquinazolinone (NU1025), CEP 9722, MK 4827, LT-673; 3-aminobenzamide; Olaparib (AZD2281; ABT-888 (Veliparib); BSI-201 (Iniparib); Rucaparib (AG-014699); INO-1001; A-966492; PJ-34; and talazoparib. In an embodiment, the PARPi may be olaparib, rucaparib, niraparib, talazoparib, veliparib, pamiparib, CEP9722, E7016, 3-Aminobenzamide or combinations thereof.

Examples of NAMPT inhibitors include AP0866 (FK866), OHS-828 (GMX1778), GMX1777, KPT-9274 (ATG-019), OT-82, LSN3154567, GNE-618 GNE-617, GNE-643, pRib-GNE617, pRib-GNE618, CB30865, A-1293201, STF-118804 AU-315, GENZ-682945, Cpds 1-14 in Table 1 in Sampath et al. (Pharmacol Rev. 2015 Jul;151:16-31. doi: 10.1016/j.pharmthera.2015.02.004. Epub 2015 Feb 21, which table is incorporated herein by reference).

Examples of CD38 inhibitors include daratumumab, isatuximab, CAR-Ts against CD38 (sorrento), GBR 1342, TAK-079, TAK-169, 78c, and apigenin.

Examples of HDAC4 inhibitors include voriostat, romidepsin, belinostat, Panobinostat, valproic acid, and entinostat.

Examples of SHP2 inhibitors include the SHP2 inhibitors disclosed in PCT/M2015/050345 (published as W02015107495), PCT/IB2015050344 (published as W02015107495), PCT/M2015/050343 (published as W02015107493), U.S. publication no. 20170342078, Xie et al., (J. Medicinal Chem., DOI: 10.1021/acs.jmedchem.7b01520, November 2017), LaRochelle et al., (25(24): 6479-6485, 2017). The listing and descriptions of SHP2 inhibitors from these published applications and publications are incorporated herein by reference. Examples of SHP2 inhibitors include, but are not limited to, TN0155, 14446-bromonaphthalen-2-yl)thiazol-2-yl)-4-methylpiperidin-4-amine, and chemical compounds having a benzothiazolopyrimidones scaffold, NSC-117199, SPI-112, SPI-112Me, Fumosorinone, demethylincisterol $A_3$, 11a-1, and Cryptotanshinone, RMC-3943, RMC-4550, SHP099, NSC-87877, RMC-4630, SPI112, BBP-398, JAB-3068, RLY-1971/GDC-1971, ERAS-601, and SH3809. Expression of the gene PTPN11 encoding SHP2 can also be inhibited by the use of inhibitory RNAs, such as siRNA, shRNA, CRISPR/Cas9 or other gene expression disrupters. Generally, an amount of from 1 µg/kg to 100 mg/kg and all values therebetween may be used.

Examples of CXCR1 inhibitors include SX-682, MK-7123, AZD5069, danirixin/GSK1325756, ladarixin, and DF2156A.

Expression of the genes encoding NAMPT, CD38, HDAC4, PARP, SHP2 and CXCR1/2 can alternatively or additionally be carried out by using inhibitory RNAs, such as siRNA, shRNA, CRISPR/Cas9 or other gene expression disrupters. For example, expression of the gene PTPN11 encoding SHP2 can be inhibited by the use of inhibitory RNAs, such as siRNA, shRNA, CRISPR/Cas9 or other gene expression disrupters.

Immune based therapies that may be used in the combination therapy (e.g., in combination with NAMPT, CD38, HDAC4, SHP2, CXCR1/2 and/or PARP inhibitors), include immune checkpoint inhibitors (e.g., anti-PD-1, anti-PD-L1, anti-CTLA-4, etc.), immune population inhibitors (e.g., neutrophils) which may be small molecule inhibitors or monoclonal antibodies, vaccines (e.g., dendritic cell-based; viral-based; autologous whole tumor cell), adoptive cellular therapy (e.g., TILs; T cell receptor-engineered lymphocytes; CAR T cells or CAR NK cells) and immune system modulators.

Immune checkpoint inhibitors may include targeting one or more immune checkpoints, including, but not limited to, PD-1/PD-L1, CTLA-4, OX40, LAG-3, TIM-3, and B7-H3. PD-1/PD-L1 and TIM-3 suppress normal T-cell activation and function. The programmed death receptor 1 (PD-1) is a T-cell surface receptor that is expressed on T cells, B cells, natural killer cells (NK), activated monocytes and dendritic cells. The role of PD-1 in normal human physiology is to limit autoimmunity by acting as a co-inhibitory immune checkpoint expressed on the surface of T cells and other immune cells, including tumor-infiltrating lymphocytes. It has two ligands: programmed death receptor ligand 1 (PD-L1/B7-H1) and 2 (PD-L2/B7-DC). CTLA-4 and B7-H3 are considered to inhibit T-cell function and become overexpressed in most solid cancers such as breast cancer, prostate cancer, renal cell carcinoma, liver cancer and brain cancer. LAG-3 is a surface molecule that promotes activation of T-cells. OX40 is a surface molecule in the tumor necrosis factor receptor family.

Several small molecules are known to inhibit various immune checkpoints. Small molecule inhibitors (SMI) that affect PD-1/PD-L1, include BMS-8, BMS-37, BMS-202, BMS-230, BMS-242, BMS-1001 and BMS-1166, SB415286, vorinostat, panobinostat, azacitidine, decitabine, entitostat, JQ1, I-BET151, GSK503. SMIs that affect CTLA4 include entitostat, panobinostat, ACY-241, azacytidine. SMIs that affect OXO include PF-04518600, ABBV-368, DB36, DB71, DB15, CVN, MGCD0103, SNDX-275, azacytidine. Small molecule inhibitors that affect LAG-3 include TSR-033, IMP32, BMS986016. Small molecule inhibitors that affect TIM-3 include TSR-022, Sym023, ATIK2a, and SMIs that affect B7-H3 include c-MYC SMIs, vorinostat, DZNep (Smith et al., Am J. Transl. Res.2019, 11(2):529-541, the relevant disclosure of which is incorporated herein by reference).

Monoclonal antibodies against immune checkpoints include antibody therapies directed against immune checkpoints PD-1 (e.g., nivolumab, pembrolizumab, cemiplimab, pidilizumab, duralumab), PD-L1 (e.g., atezolizumab, durvalumab, avelumab), CTLA-4 (e.g., ipilimumab, tremelimumab), and immune-activating antibodies (e.g., directed against 41BB (e.g., utomilumab).

Examples of T cell-based immunotherapies include adoptive cell transfer therapies in which patients are infused with their own immune cells (e.g., T cells include enriched populations of tumor-reactive T cells, genetically-engineered CAR-T cells (chimeric antigen receptor T cells) or T cell receptor-engineered T cells, and natural killer cells (NK cells; FATE-NK100)).

Cancer vaccines including vaccines based on tumor cells or tumor associated antigens, dendritic cell (DC)-based vaccines, and oncolytic virus therapy.

Immune system modulators can include cytokines, such as interferons, and interleukins, BCG, immunomodulatory drugs, such as Thalidomide, Lenalidomide, Pomalidomide, and Imiquimod.

Generally, a therapeutically effective amount of an antibody, small molecules, or other compounds or compositions described herein (e.g., inhibitors of NAMPT, CD38, HDAC4, PARP, SHP2 and CXCR1/2 and immune therapy (e.g., checkpoint inhibitor)) can be in the range of 1.0 µg/kg to 100 mg/kg and all values and ranges therebetween. For example, an antibody, small molecule, or other compounds may be in the range of 0.01 mg/kg to 100 mg/kg and all values therebetween. For example, the antibody, small molecule or compounds can be 0.1 mg/kg to 100 mg/kg, 0.1 mg/kg to 50 mg/kg etc. The NAMPT, CD38, HDAC4, PARP, SHP2 and CXCR1/2 inhibitor(s) and the immune therapy (e.g., checkpoint inhibitor) may be administered in separate compositions or in the same composition, via the same route or separate routes, over a same period of time or different periods of time. The two administrations regimens may overlap partially or completely or not at all. The compositions may comprise a pharmaceutically acceptable carrier or excipient, which typically does not produce an adverse, allergic or undesirable reaction when administered to an individual, such as a human subject. Pharmaceutically acceptable carrier or excipient may be fillers (solids, liquids, semi-solids), diluents, encapsulating materials and the like. Examples include, but are not limited to, saline, buffered saline, dextrose, water, glycerol, ethanol, etc.

The pharmaceutical compositions may be in the form of solutions, suspensions, emulsions, and solid injectable compositions that are dissolved or suspended in a solvent immediately before use. The injections may be prepared by dissolving, suspending or emulsifying one or more of the active ingredients in a diluent. Examples of diluents are distilled water for injection, physiological saline, physiologic buffer, vegetable oil, alcohol, and a combination thereof. Further, the compositions may contain stabilizers, solubilizers, suspending agents, emulsifiers, soothing agents, buffers, preservatives, etc. The pharmaceutical compositions may be formulated into a sterile solid or powdered preparation, for example, by freeze-drying, and may be used after sterilized or dissolved in sterile injectable water or other sterile diluent(s) immediately before use. The compositions can include one or more standard pharmaceutically acceptable carriers. Some examples herein of pharmaceutically acceptable carriers can be found in: *Remington: The Science and Practice of Pharmacy* (2013) 22nd Edition, Pharmaceutical Press.

The pharmaceutical compositions of the invention may be administered via any route that is appropriate, including but not limited to oral, parenteral, sublingual, transdermal, rectal, transmucosal, topical, via inhalation, via buccal administration, or combinations thereof. Parenteral administration includes, but is not limited to, intravenous, intraarterial, intraperitoneal, subcutaneous, intratumoral, intramuscular, intrathecal, and intraarticular. The agents(s) can also be administered in the form of an implant, which allows a slow release of the compound(s), as well as a slow controlled i.v. infusion. The NAMPT, CD38, HDAC4, PARP, SHP2 and CXCR1/2 inhibitors and the immune therapy may be delivered via different routes or the same route. The one or more inhibitors of NAMPT, CD38, HDAC4, PARP, SHP2 and CXCR1/2, and immune based therapy may be administered at the same or different times, over the same period of time or different periods of time, by the same route or different routes, concurrently or sequentially, or overlapping, or any combination of administration regimens and routes.

Individuals who may receive the combination treatment described herein include those afflicted with or diagnosed with a cancer in which the cells are deficient in LKB1, or deficient in LKB1 and carry a mutation in KRAS (such as a constitutively active mutation). Examples include any type of tumor as well as blood cancers. Examples include but are not limited to, breast cancer, lung cancer, which may be non-small cell lung cancer (NSCLC). The NSCLC may be squamous cell (or epidermoid) carcinoma, adenocarcinoma and, large cell (or undifferentiated) carcinoma, or any other type, melanoma of the skin, kidney cancer, bladder cancer, liver cancer, pancreatic cancer, colon cancer, head and neck cancers, prostate cancer, ovarian cancer, cervical cancer, Hodgkin lymphoma, urinary tract cancers, and other types of cancers. The cancer, such as lung cancer or breast cancer may be refractory to current treatments. The breast cancer may be metastatic triple-negative breast cancer, all stages, and may be refractory to current treatments.

In an embodiment, the one or more NAMPT, CD38, HDAC4, PARP, SHP2 and/or CXCR1/2 inhibitor(s) may be administered first and then after a suitable period of time (such as hours, days or weeks), the immune therapy may be administered. In an embodiment, after the administration of NAMPT, CD38, HDAC4, PARP, SHP2 and/or CXCR1/2 inhibitor(s), the cells may be tested for upregulation of immune checkpoints, such as PD-1 or PD-L1. If these are found to be upregulated compared to a control value (such as value prior to administration of NAMPT, CD38, HDAC4, PARP, SHP2 and/or CXCR1/2 inhibitor(s)), or a value from normal individuals, then the immune therapy can be initiated. The PD-1 and PD-L1 levels may be detected by conventional techniques.

In an aspect, this disclosure provides kits for the treatment of cancer. The kit may comprise in a single or separate compositions: i) one or more of NAMPT, CD38, HDAC4, PARP, SHP2 and/or CXCR1/2 inhibitors, and ii) an immune checkpoint inhibitor, and optionally, means for testing if checkpoint inhibitors, such as, PD-1 or PD-L1 are upregulated. Buffers and instructions for administration may also be provided.

The following example is provided to illustrate the invention and is not intended to be restrictive.

EXAMPLE 1

Materials and Methods

Cell Culture

Lung cancer cell lines were cultured in RPMI 1640 (Gibco, Thermo Fisher Scientific) supplemented with 10% fetal bovine serum (FBS, Gibco). The KPC Kras$^{LA1-G12D}$ p53$^{-/-}$ (KP) and KLA Kras$^{LA1-G12D}$;Lkb1$^{-/-}$ (KL) murine lung cancer cell lines were generated by dissociation of KP and KL lung tumor nodules to single cell suspensions, seeded on tissue culture plates, and cultured in RPMI 1640 (Gibco, Thermo Fisher Scientific) supplemented with 10% fetal bovine serum (FBS, Gibco). HEK-293 cells were obtained from ATCC and cultured in DMEM (Gibco) supplemented with 10% FBS. All cells were cultured at 37° C. in a humidified incubator at 5% $CO_2$ and verified on a weekly basis to be mycoplasma negative.

Plasmids, Transfections, and Lentiviral Generation and Transduction

Cas9 expression constructs were cloned into the pCDH-CMV vector using primer sequences listed the methods from our prior publication. Guide RNA's targeting SIK1, SIK2, SIK3, or SIK1/2/3 were cloned into pX458-RFP vector. Stable cell lines were generated using lentiviral transduction, which were first generated by co-transfecting packaging vector psPAX2, envelope vector pMD2.G, and the expression vectors into HEK-293 cells using Lipofectamine 3000. Transfection medium was removed and HEK-293 cells were cultured in RPMI 1640+10% FBS for 48 hours. Viruses were then syringe-filtered through a 0.45 μm nylon filter and Polybrene (Santa Cruz) was added to a final concentration of 8 μg/mL. Medium containing lentiviruses was then added to cells, left to allow infection of the cells for 48 hours, and replaced with fresh medium for further experiments. Cells expressing the constructs were selected for with Puromycin and Blasticidin.

Mice Experiments

All animal experiments were reviewed and approved by the Institutional Animal Care and Use Committee (IACUC) at NYU Langone Health. For lung tumor growth assays, $10^6$ KP and KL syngeneic mouse lung cancer cells were implanted into male C57BL/6 mice at 7 weeks of age via tail vein injection. After 8 weeks, mice were imaged by MRI to assess tumor volume. For drug treatment experiments, $10^6$ KLA cells were injected subcutaneously in the right flank of female C57BL/6 mice at 7 weeks of age or injected via tail vein injection. Once tumors reached ~150–200 mm$^3$ in volume (or 50–100 mm$^3$), mice were dosed with 40 mg/kg (or 10 mg/kg) mouse weight of the NAMPT inhibitor FK 866 (MedChemExpress) for 5 days/week by intraperitoneal (I.P.) injection, 200 μg anti-PD-1 antibody (BioXcell) weekly per mouse by I.P., or both drugs in combination. SHP2 inhibitor SHP099 (MedChemExpress) were administered with 75 mg/kg via oral gavage injection daily, and CXCR1/2 inhibitor SX-682 (Syntrix) were administered at 100 mg/kg via oral gavage injection daily, alone or in combination with FK866. Tumor volumes were measured using digital calipers or MRI. Mouse weights were measured weekly to adjust total dosage and assess the effects of drug combinations on mouse health. After euthanasia by $CO_2$ exposure at 3 L/min, syngeneic primary tumors and/or mouse lungs were formalin-fixed, paraffin-embedded, and sectioned for histological analysis. For animal studies, to test the hypothesis that effective combinatorial treatment would reduce primary tumor growth by at least 30% with a variance of 10%, the minimal sample size for 90% power with statistical significance accepted at α=0.05 was four mice per experimental group.

Western Blotting and qPCR

Protein lysates were boiled in 5×SDS sample buffer with bromophenol blue for 10 minutes, placed on ice for 10 minutes, separated by SDS-PAGE, transferred to nitrocellulose membranes, and probed with collagen I antibody (Abcam, ab34710). Total RNA was isolated from cells by TRIzol (Thermo) according to manufacturer protocol and cDNA was generated using qSCRIPT reagents (Quanta). QPCR assays were performed using SYBR Green PCR Master Mix (Thermo) along with primers listed in the Supplementary Methods and normalized to the L32 gene.

Flow Cytometry

Tumors were mechanically dissociated followed by enzymatic digestion in RPMI 1640 containing 2 U/mL DNAse and 0.5% w/v collagenase type V at 37° C. for 45 minutes and tumor cell suspensions were filtered through a 70 μm Falcon Nylon cell strainer (Fisher Scientific). Spleens were mechanically dissociated and filtered through a 40 μm Falcon Nylon cell strainer and rinsed with RPMI 1640. Bone marrow derived cells (BMDC) were isolated by straining 10 mL PBS+1 mM EDTA through mice femurs. All cell suspensions were centrifuged at 2,000 rpm for 5 minutes and resuspended in RBC lysis buffer (Biolegend) for 5 minutes at room temperature. RBC lysis was halted by the addition of PBS and cells were centrifuged and resuspended in FACS buffer (PBS+2% FBS+1 mM EDTA). Splenocytes were used for further in vitro co-culture assays. Tumor cell suspensions were counted and 2×$10^6$ tumor cells per sample were probed with the indicated fluorescently labeled antibodies. Intracellular stains were performed by fixing cells in 1% paraformaldehyde and permeabilizing cells in permeabilization buffer (BD Biosciences) for 30 minutes at room temperature. Cells were then washed and stained with indicated fluorescently labeled antibodies. FlowJo 10.6.1 was used to analyze FACS data.

Metabolomic Profiling

Mouse lung tumor nodules were resected, snap frozen in liquid nitrogen, and processed at NYU Langone Health Metabolomics Core for hybrid metabolomics profiling. Samples were first precipitated by addition of suitable amount of SOP12 extraction buffer containing isotopic internal standards to reach an extraction ratio of 10 mg of tissue per 1 mL of SOP12 extraction buffer. Then, 270 μL of the resulting sample extract was transferred to a new 1.5 mL microcentrifuge tube for speed vacuum concentration, and ultimately resolubilized in 30 μL of LCMS grade H2O for mass spectrometry analysis on the hybrid platform. Instrument performance was assessed using the internal standards added to the samples during metabolite extraction. Metabolite peak intensities were extracted according to a library of m/z values and retention times developed with authentic standards. Intensities were extracted with an in-house script with a 10 ppm tolerance for the theoretical m/z of each metabolite, and a maximum 30 sec retention time window. Statistically significant differential metabolite levels were analyzed using Python script.

Lung Cancer Patient Transcriptomic Analysis

Human lung adenocarcinoma RNA-seq data were obtained from The Cancer Genome Atlas (TCGA) publicly available database. Patient datasets with KRAS mutations were further stratified into groups with TP53 (KP) or STK11/LKB1 (KL) co-occurring mutations for downstream comparative analyses. Gene set enrichment analysis (GSEA) was used to correlate $NAD^+$ de novo and salvage pathways with TCGA RNA-seq data between KP and KL patient samples. Differential gene expression analysis on KP and KL RNA-seq data was also performed using DESeq2 R package to identify statistically significant up- and down-regulated genes.

Statistics

Unless otherwise stated above, statistics were calculated using GraphPad 8 software. Statistical significance was accepted as P-value less than 0.05 using one-way ANOVA post-hoc Tukey's test for multi-group comparisons or two-tailed student's t-test for two-group comparisons.

Results

To confirm that loss of LKB1 or the downstream SIK kinase family was necessary for promoting tumor growth in our models, we knocked out SIK1/2/3 or LKB1 in mouse lung cancer cell lines isolated from the mutant Kras,p53 genetically engineered mouse model (GEMM) of lung adenocarcinoma, and observed increased tumor size in KP allografts with SIK or LKB1 loss, comparable to tumors generated by transplanting KL cell lines derived from mutant Kras;Lkb1 GEMMS (FIG. 1A). Flow cytometry analysis of immune cell populations within the lung tumor tissues showed a consistent decrease in total macrophages, dendritic cells, and activated $CD103^+$ dendritic cells in tumors with SIK or LKB1 loss (FIG. 1B).

Figure 2:
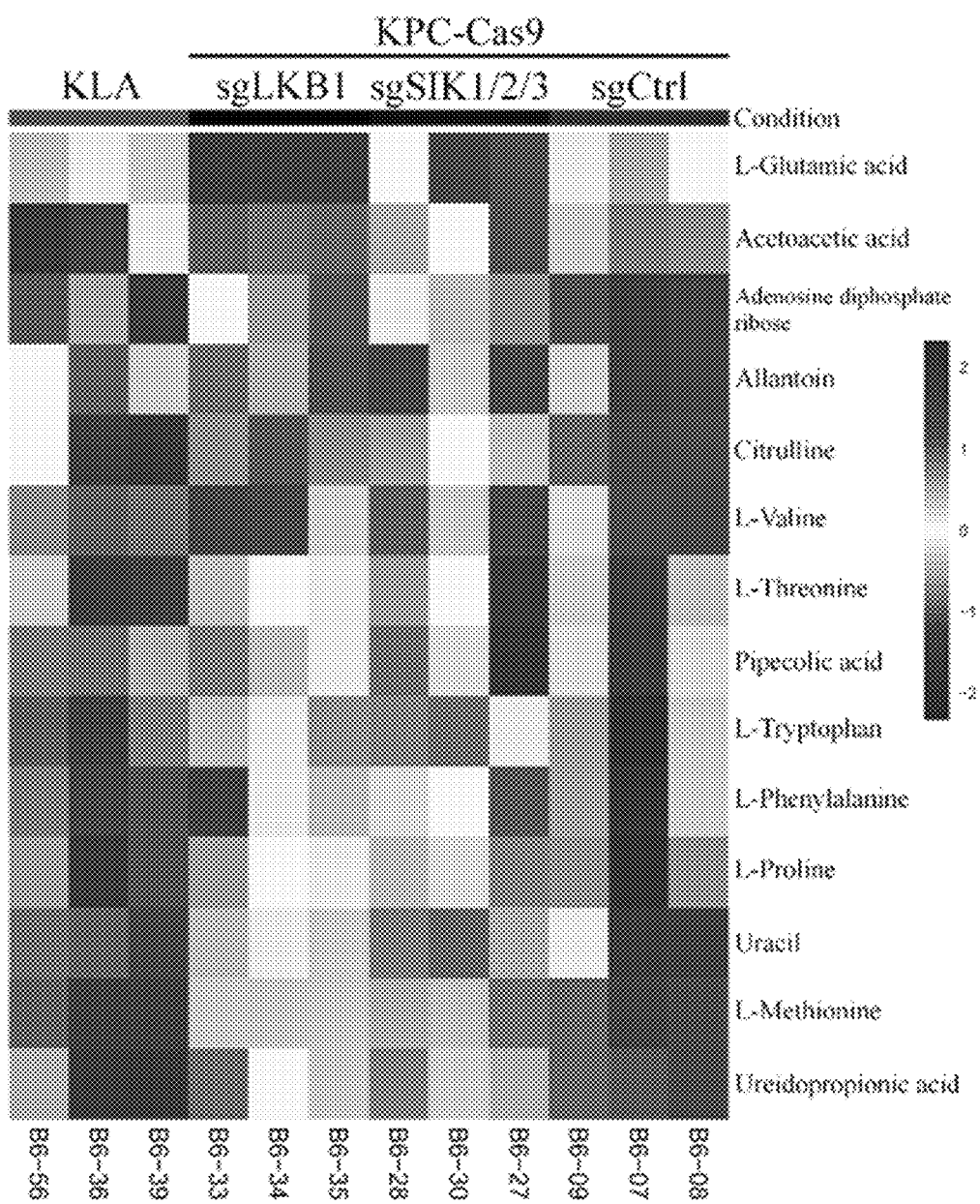
FIG. 2. Mutant LKB1 tumors exhibit increased $NAD^+$ salvage pathway signatures. A) Heatmap of statistically significant differential metabolite levels in indicated lung tumors. B) Schematic of $NAD^+$ salvage and de novo synthesis pathways. C) GSEA pathway analysis of $NAD^+$ salvage and de novo pathway gene enrichment in KL vs KP TCGA lung adenocarcinoma patient RNA-seq samples. D) Dotplots of $NAD^+$ salvage pathway genes and PD-L1 mRNA expression in TCGA KL vs KP tumors. $P<0.01$, $*P<0.001$, $****P<0.0001$.
Figure 2:
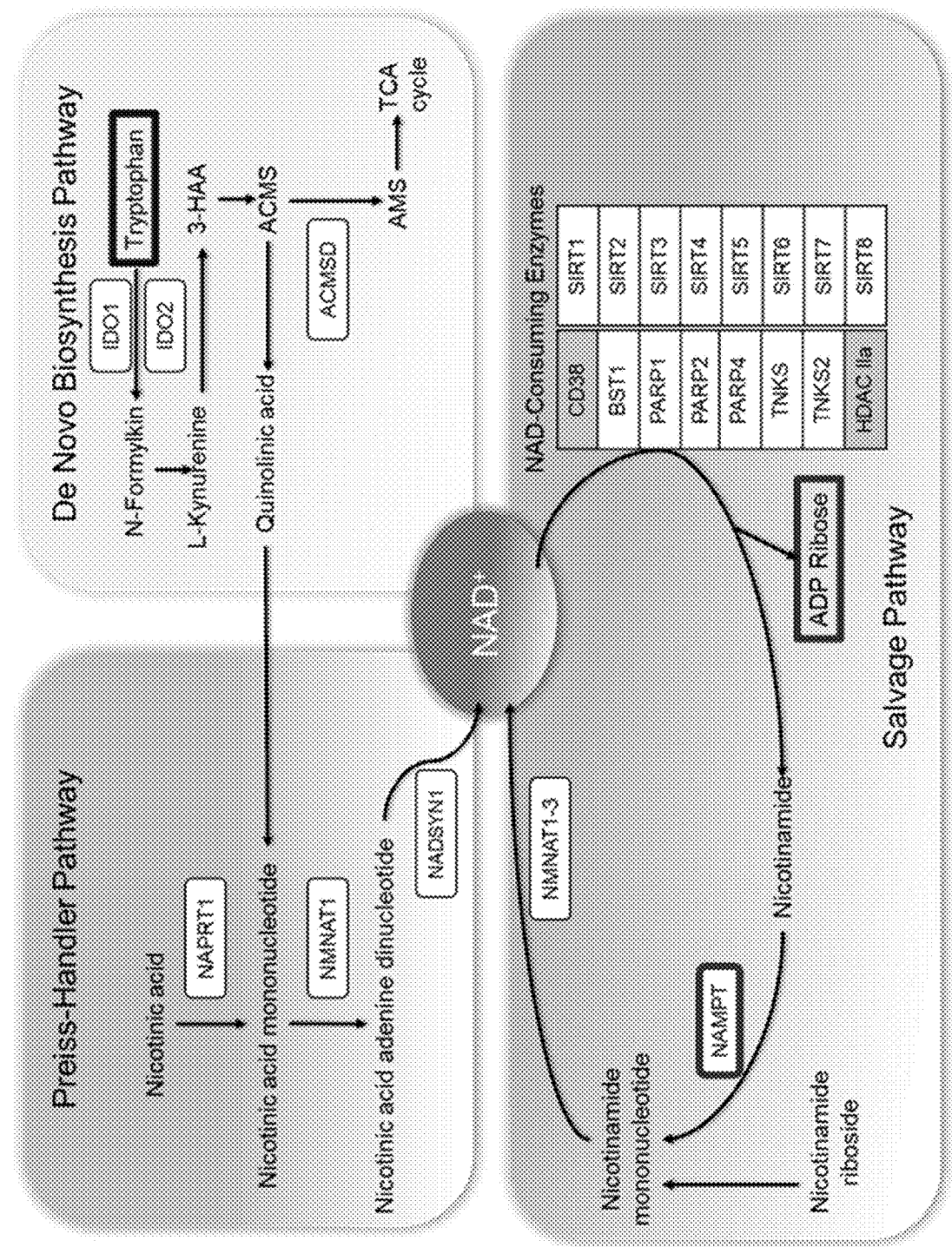
Figure 2:
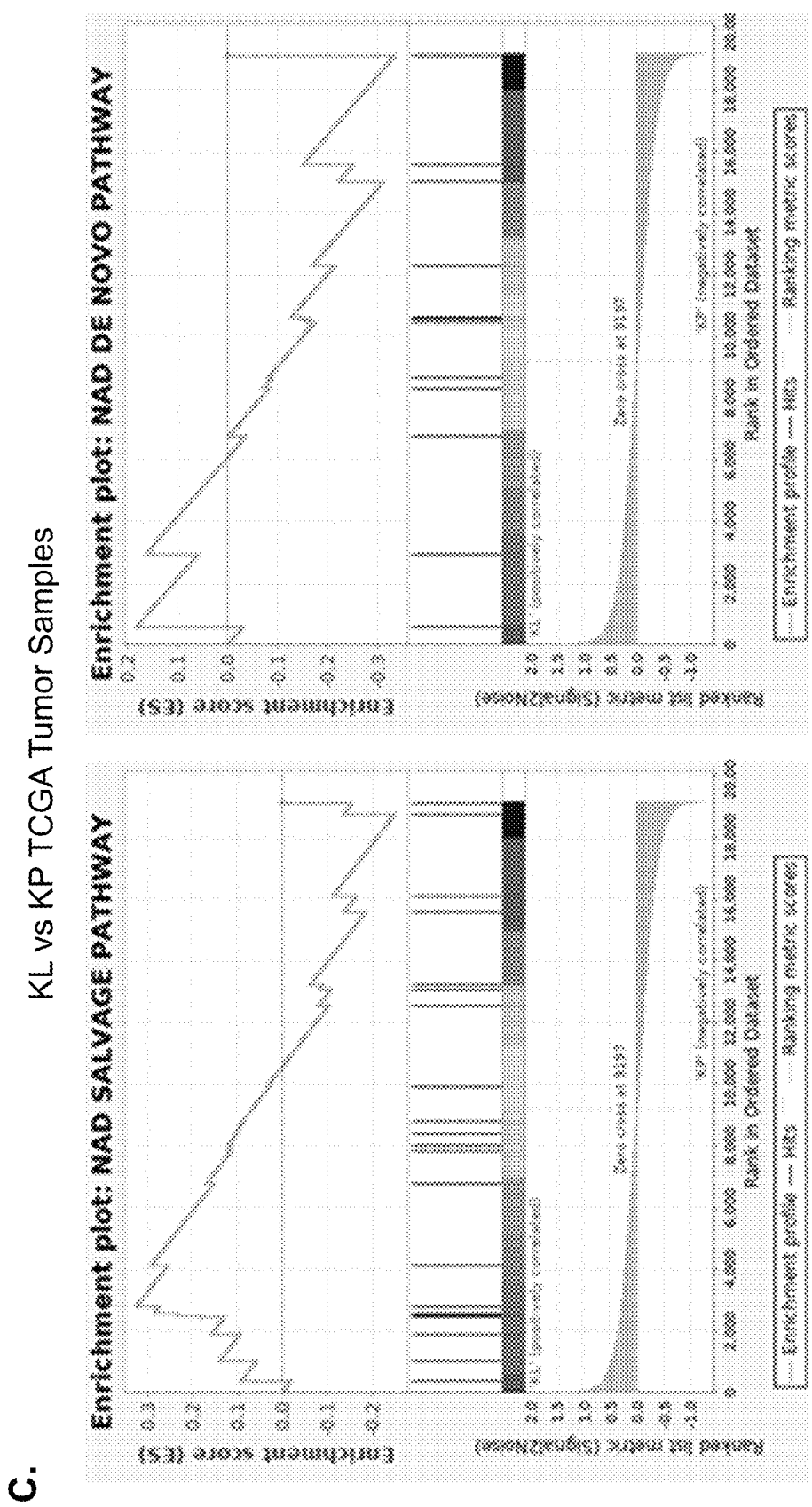
Figure 2:
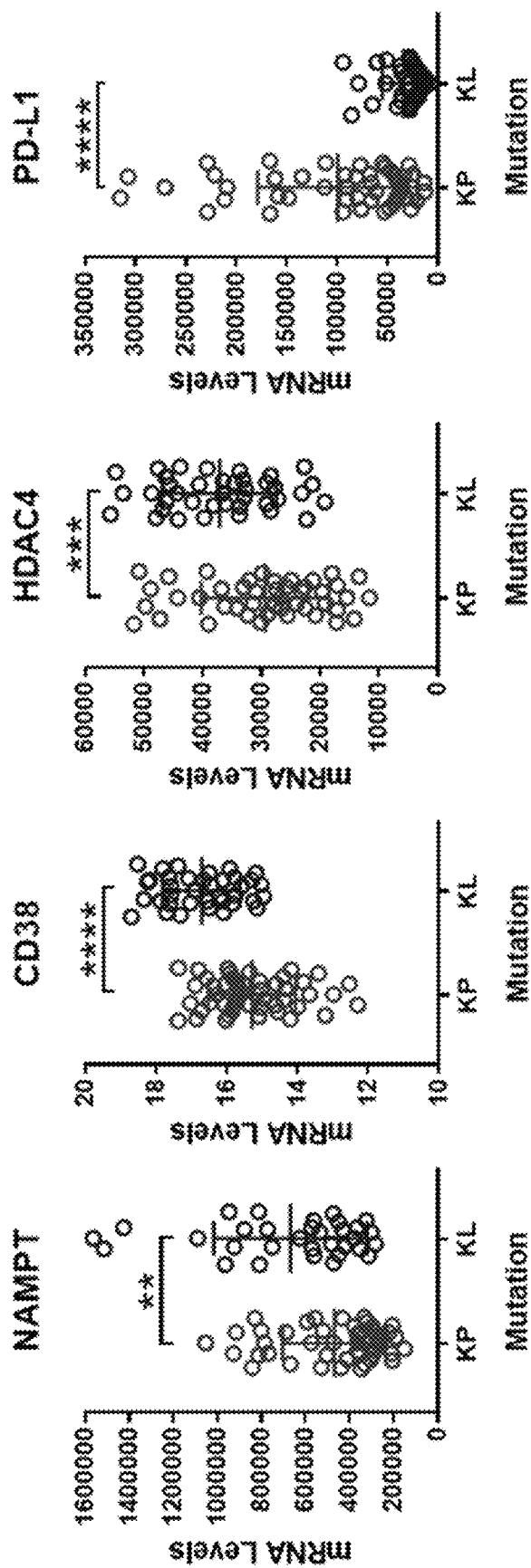
Figure 3:
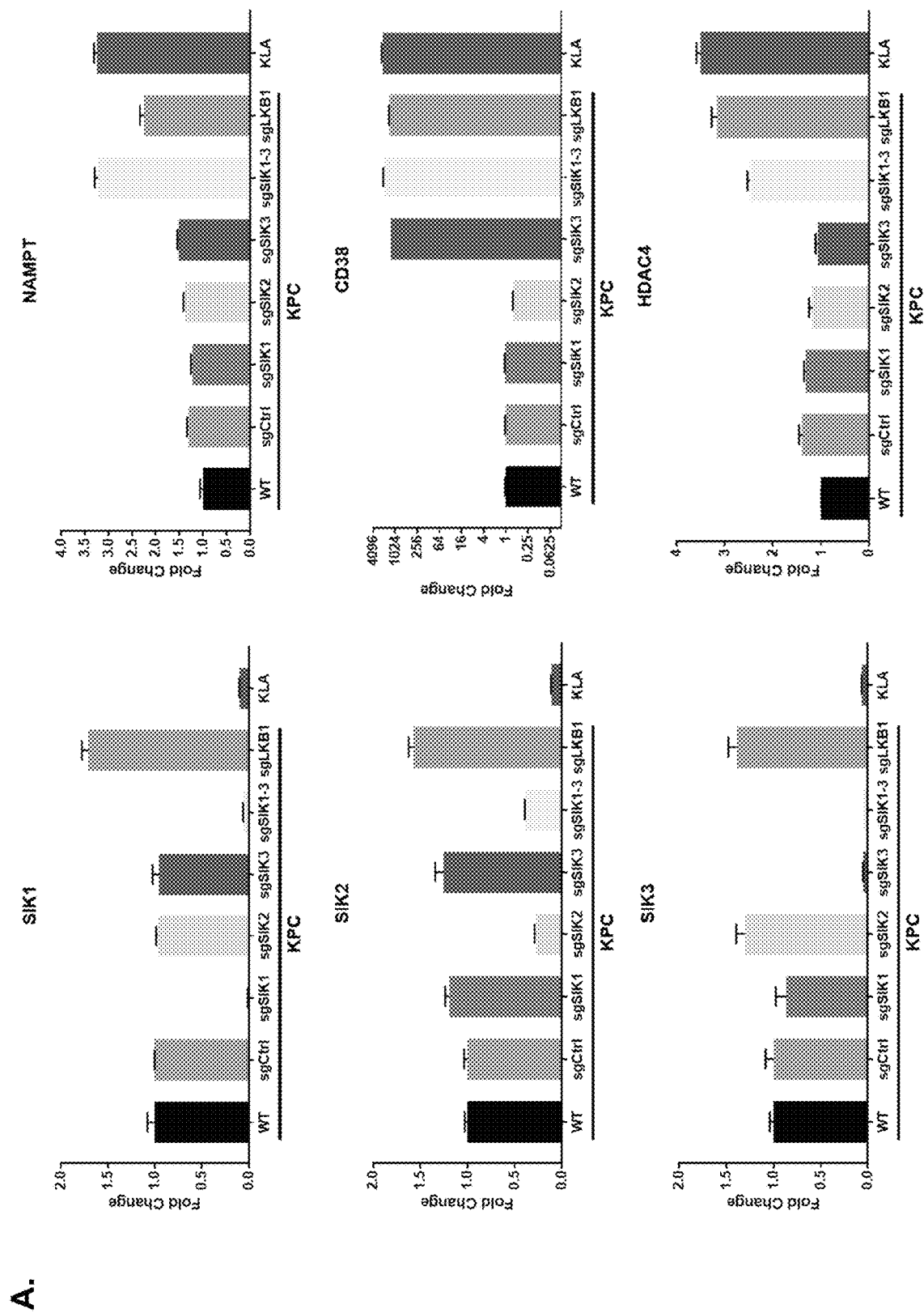
FIG. 3. SIK or LKB1 loss increases $NAD^+$ salvage pathway gene expression. A) Relative mRNA levels of indicated genes in KP cells with SIK or LKB1 knockout or KL cells. B) Western blot of indicated proteins in mouse and human lung cancer cell lines with SIK or LKB1 mutations.
Figure 3:
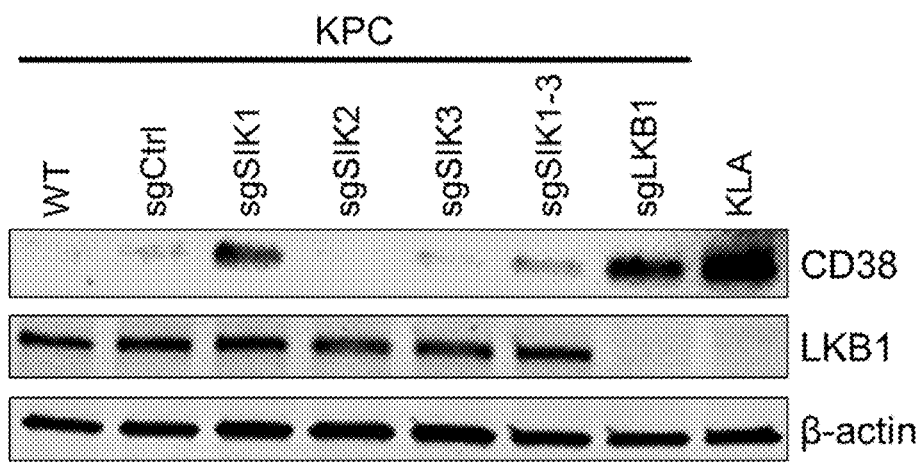
Figure 3:
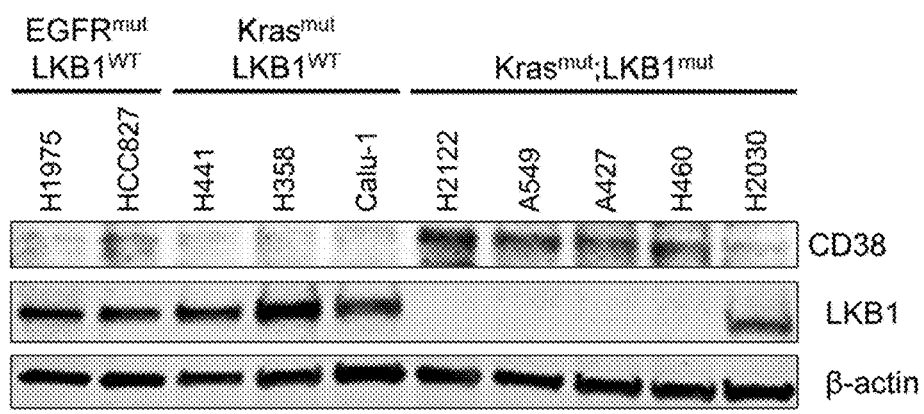

To identify specific differential metabolite levels following loss of SIK or LKB1, we performed hybrid metabolomics profiling on KP tumor tissues with SIK or LKB1 knockout or KL tumor tissues, and observed an increase in ADP ribose and a decrease in multiple amino acids including tryptophan (FIG. 2A). Our metabolomics profile suggested that KL tumors have an upregulation of $NAD^+$ salvage pathway and downregulation of $NAD^+$ de novo pathway synthesis compared to KP tumors, which was further confirmed by GSEA analysis of KL and KP TCGA human lung cancer gene expression (FIG. 2B, C). In the $NAD^+$ salvage pathway, $NAD^+$ is synthesized from nicotinamide (NAM) by NAMPT, and is then catalyzed by $NAD^+$ consuming enzymes, producing ADP ribose and NAM as byproducts (FIG. 2B). The observed increase in ADP ribose and salvage pathway genes suggested that KL tumors have an upregulation of $NAD^+$ consuming enzymes. Differential gene expression analysis of $NAD^+$ salvage pathway genes in TCGA lung cancer datasets showed increased expression in NAMPT, CD38, and HDAC4 in KL tumors compared to KP tumors, correlating with a decrease in PD-L1 expression (FIG. 2D). QPCR analysis of mouse and human lung cancer cells showed a consistent increase in salvage pathway genes following SIK or LKB1 loss (FIG. 3A, B).

Figure 4:
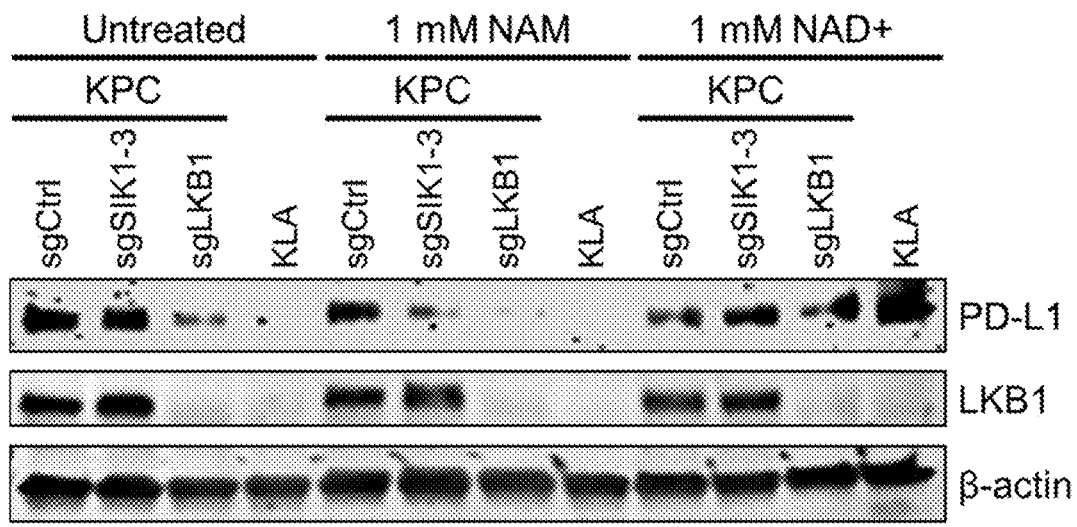
FIG. 4. Inhibition of $NAD^+$ synthesis or consumption rescues PD-L1 expression on mutant LKB1 tumor cells. A) Western blot of indicated proteins in KL or KP cells with SIK or LKB1 knockout and treated with NAM or $NAD^+$ for 6 days. B) Western blot of PD-L1 and (β-actin in KL cells following stable knockdown of NAMPT, CD38, and HDAC4. C) Top: Histogram of PD-L1$^+$ KL cells following knockdown of indicated genes. Bottom: Quantification of percentage of PD-L1$^+$ KL cells at indicated gates denoted by dotted line. $****P<0.0001$.
Figure 4:
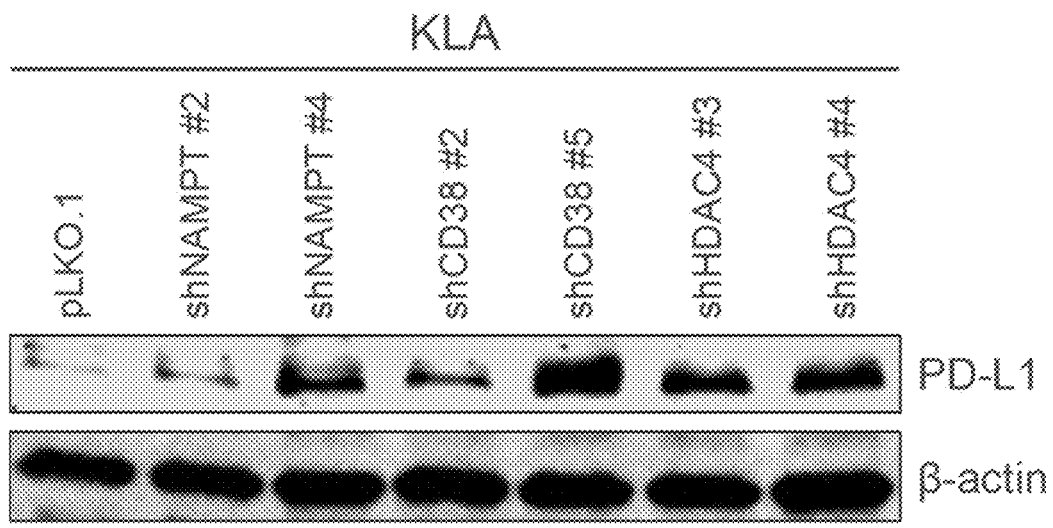
Figure 4:
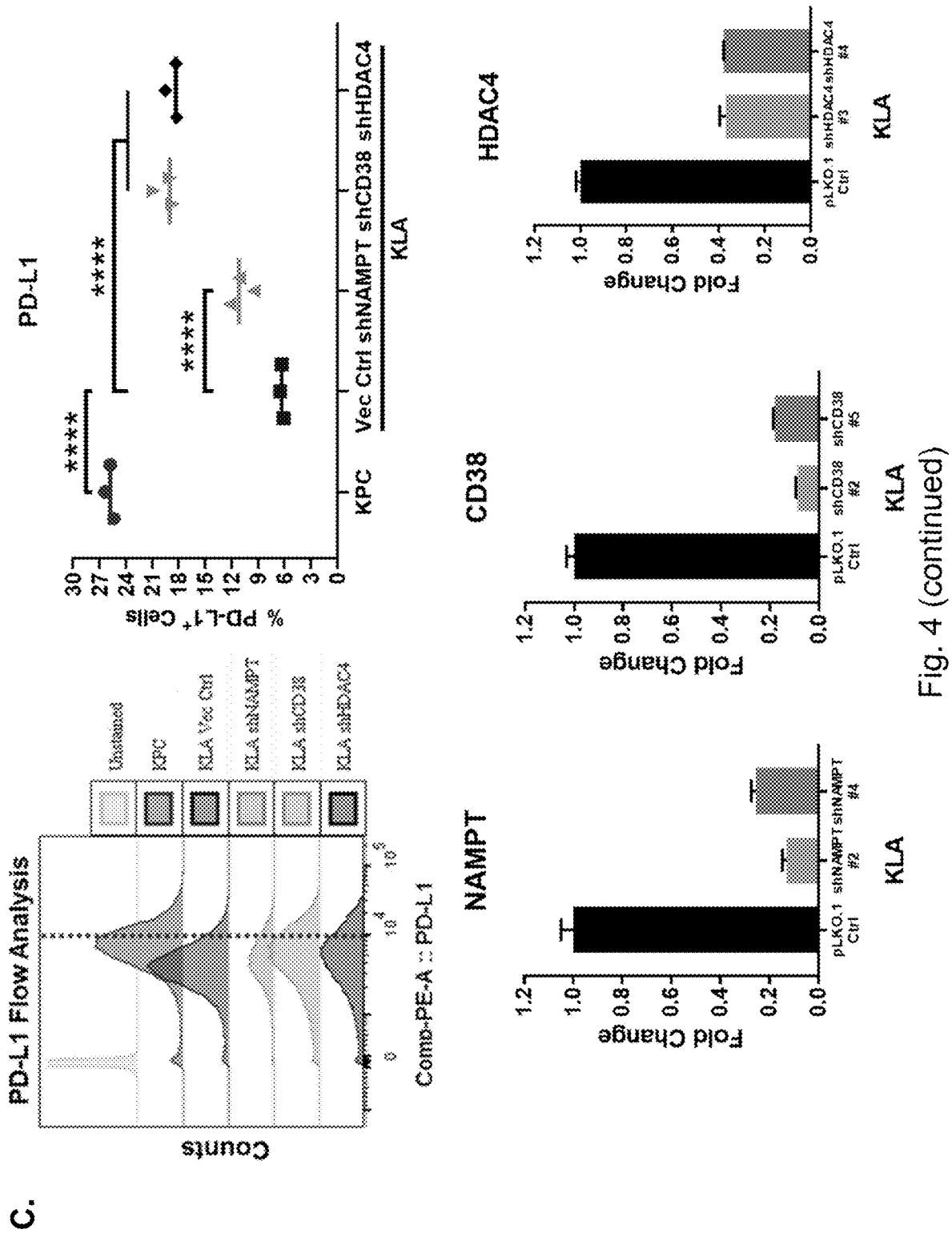
Figure 5:
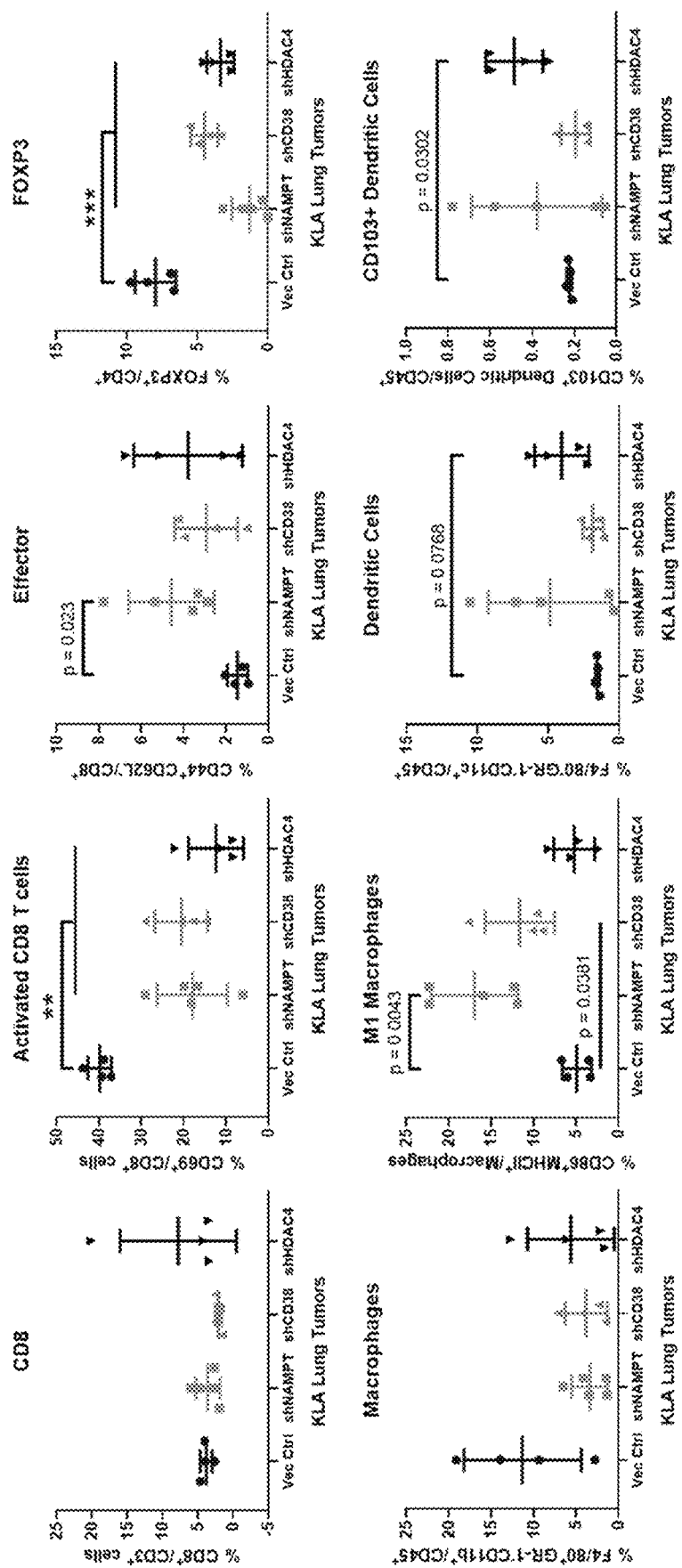
FIG. 5. Inhibition of $NAD^+$ synthesis or consumption pro-inflammatory immune microenvironment in KL tumors. Flow cytometry analysis of indicated immune populations in KL allograft tumors with stable knockdown of NAMPT, CD38, or HDAC4. $**P<0.01$.
Figure 6:
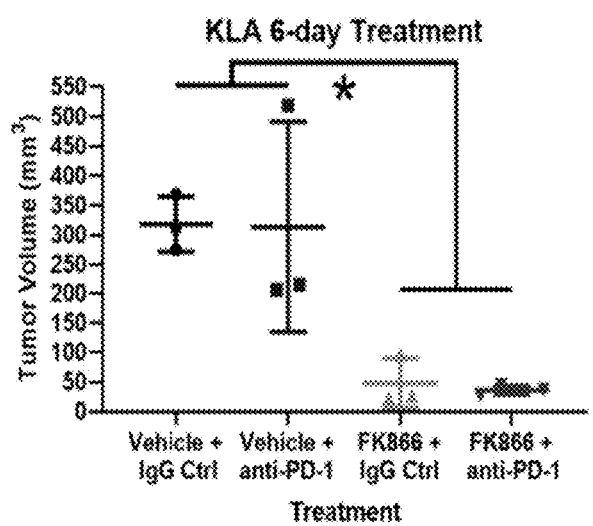
FIG. 6. NAMPT inhibition reduced KL lung tumor growth in vivo. A) Lung tumor volume measurements of KL subcutaneous allograft tumors following treatment with indicated drugs. B) Average tumor volumes over time in KL tumors with indicated treatments. Arrow denotes treatment start time. C) Percent change in KL tumor volume after 6 days of treatment with indicated drugs. D) Images of subcutaneous KL tumor allografts at endpoint of treatment experiment. *P<0.05.
Figure 6:
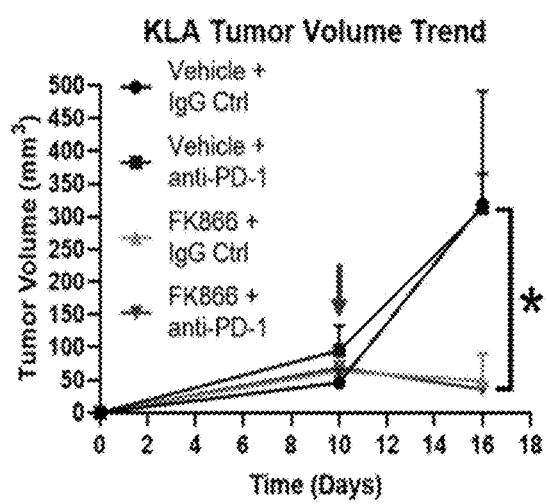
Figure 6:
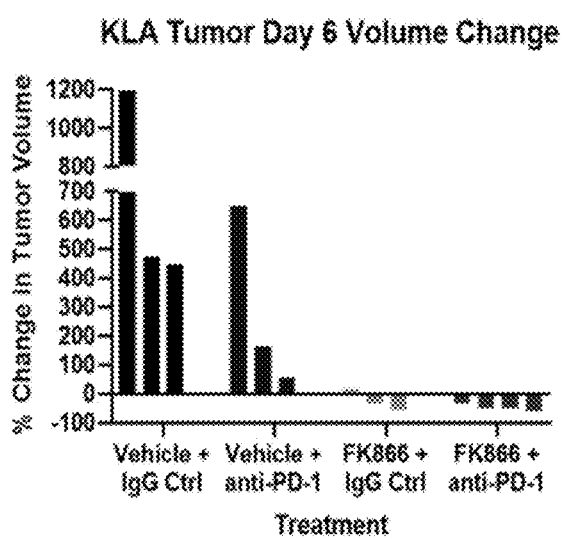
Figure 6:
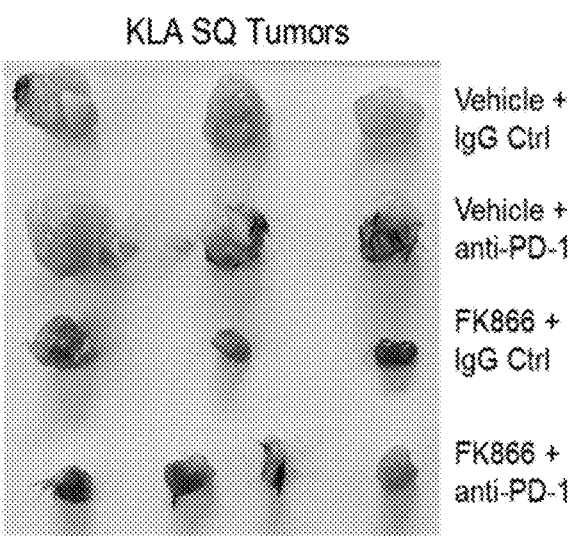

Although PD-L1 expression has been shown to be negatively correlated with LKB1 loss, the mechanism of PD-L1 regulation by LKB1 has not been well-defined. Since ADP ribose and HDAC4 can epigenetically regulate gene expression, we next sought to determine if byproducts of the $NAD^+$ salvage pathway regulate PD-L1 expression. Western blot analysis of KP cells with SIK or LKB1 knockout did not show a decrease in baseline PD-L1 levels to similar degrees as KL cells (FIG. 4A). However, following NAM treatment, the precursor to $NAD^+$, KP cells with SIK or LKB1 KO showed a marked reduction in PD-L1 levels while NAM had no effect on PD-L1 levels in KP cells with wild-type SIK or LKB1 (FIG. 4A). Consistent with this observation, stable knockdown of NAMPT to restrict $NAD^+$ synthesis or knockdown of CD38 and HDAC4 to inhibit $NAD^+$ consumption increased PD-L1 expression on KL tumor cells as assessed by Western blotting and flow cytometry (FIG. 4B, C). Additionally, knockdown of NAMPT, CD38, and HDAC4 promoted a more pro-inflammatory immune microenvironment in KL tumors as characterized by increased effector $CD8^+$ T cells, M1 macrophages, total dendritic cells, and activated $CD103^+$ dendritic cells, with a decrease in $FOXP3^+$ regulatory $CD4^+$ T cells (FIG. 5). Furthermore, knockdown of NAMPT, CD38, and HDAC4 in KL allografts also decreased overall lung tumor burden (data not shown).

Based on our findings, we next sought to determine if therapeutic inhibition of NAMPT synergized with PD-1 blockade. Treatment of KL allograft tumor implanted subcutaneously in the right flank of syngeneic wild-type (WT) mice with the NAMPT inhibitor FK866 or anti-PD-1 as monotherapies or in combination showed that single-agent FK866 reduced lung tumor growth only after 6 days of treatment (FIG. 6A-D).

Figure 7:
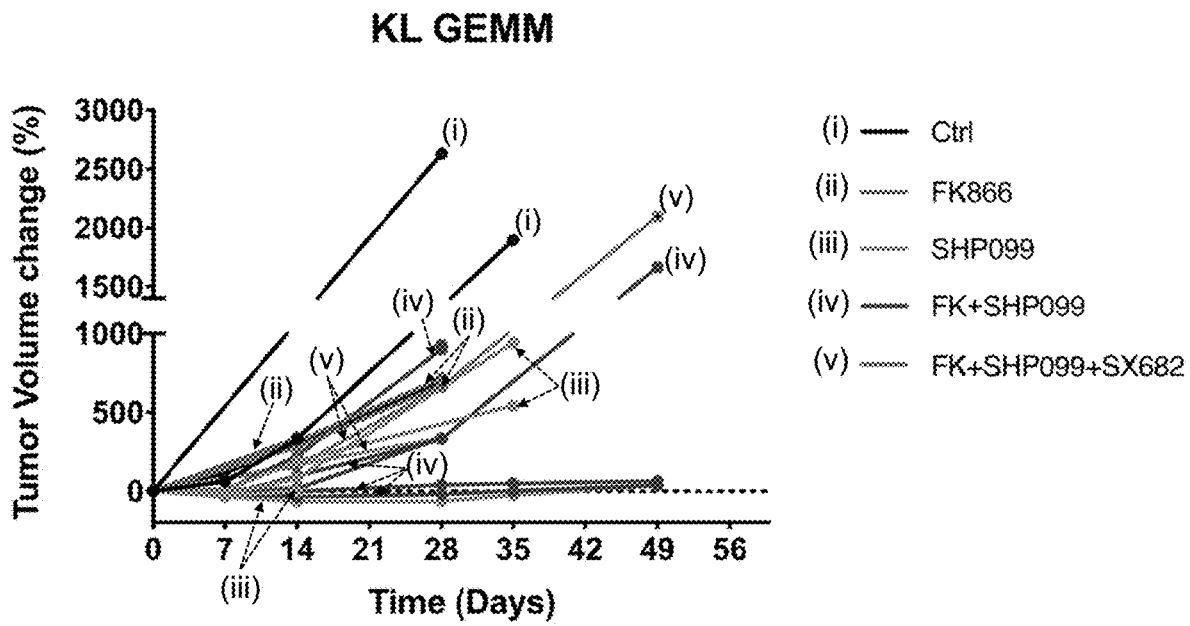
FIG. 7. NAMPT inhibition reduced KL lung tumor growth in vivo. A) Lung tumor volume measurements of KL GEMM tumors following treatment with indicated drugs. B) Lung tumor volume changes 2 weeks after indicated drug treatment using KL allograft tumors. C) FACS analysis of tumor immune infiltrates from KL allograft tumors after indicated drug treatment.
Figure 7:
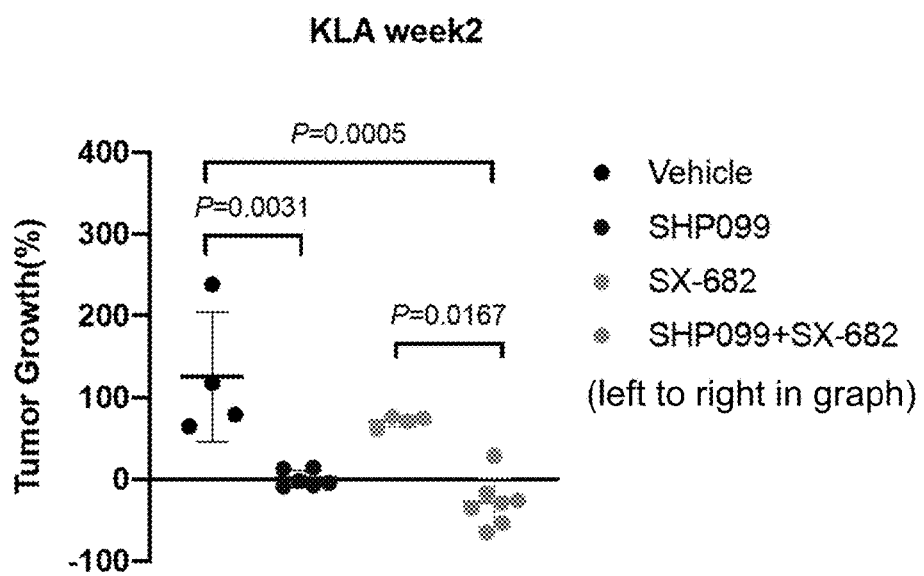
Figure 7:
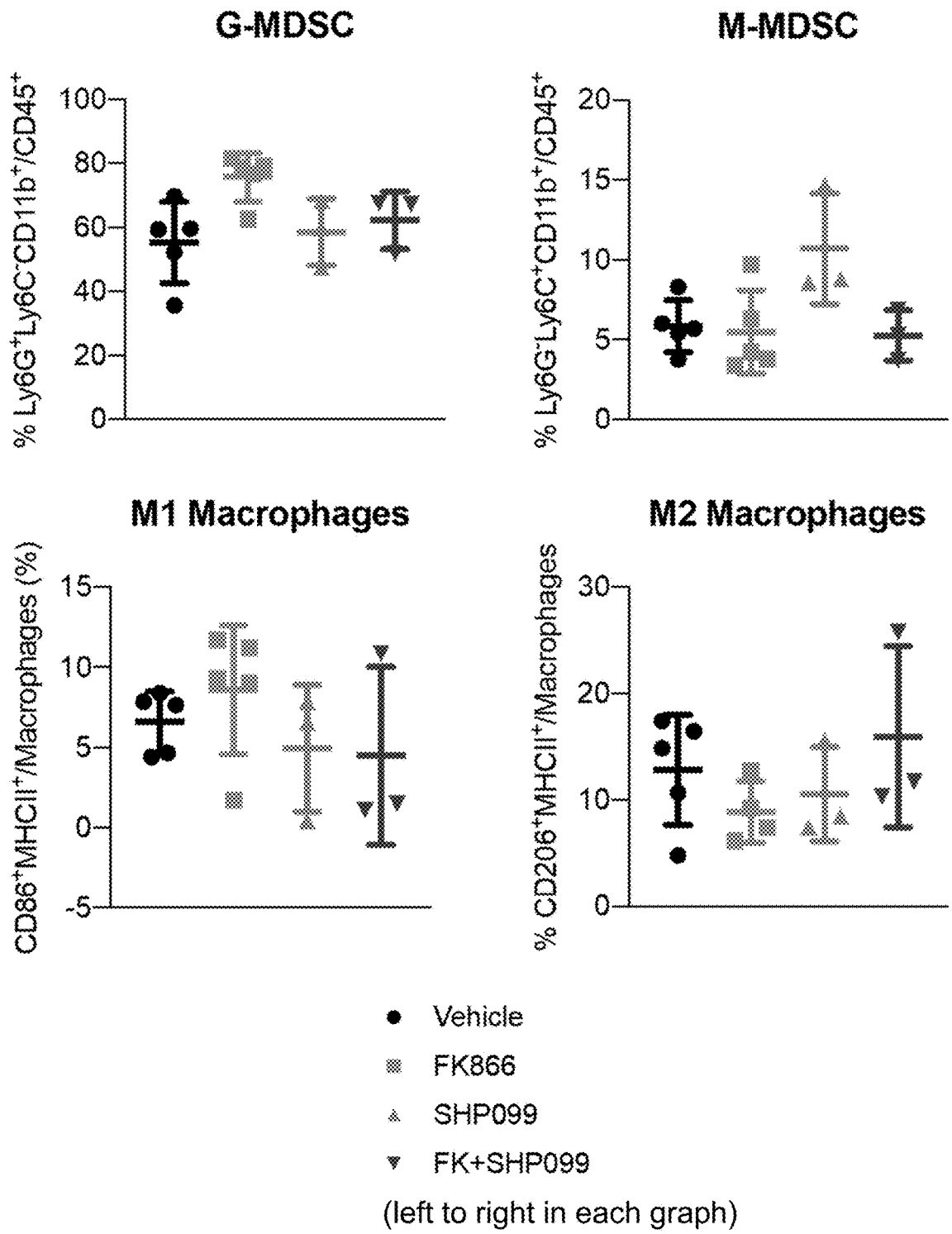

Next, we next sought to determine if therapeutic inhibition of NAMPT inhibition synergized with other drug combinations. Treatment of KL GEMM lung tumors with the NAMPT inhibitor FK866 together with SHP2 inhibitor SHP099 and CXCR2inhibitor SX682 showed that LKB1 mutant tumors has reduced growth upon treatment. In addition, FK866 and SHP099 treatment reduced KL allograft tumor growth in the lung, this is due to cell autonomous growth inhibition of tumor cells as well as immune stimulating effect in the tumor microenvironment (FIG. 7A-C).

Our findings demonstrate a mechanism by which $NAD^+$ synthesis and consumption by the salvage pathway epigenetically suppresses PD-L1 expression in mutant KRAS; LKB1 lung cancers to promote resistance to immune checkpoint blockade therapies. Inhibition of the upregulated components of the $NAD^+$ salvage pathway rescued PD-L1 expression and reduced lung tumor growth. Our study identifies and validates multiple potential therapeutic targets to inhibit mutant LKB1 lung cancers and abrogate resistance to immune checkpoint blockade therapies.

While the invention has been described through embodiments, routine modifications to the disclosure here will be apparent to those skilled in the art. Such modifications are intended to be within the scope of this disclosure.

What is claimed is:

1. A method for treatment of cancer, wherein the cancer cells are LKB1 deficient, the method comprising administering to an individual in need of treatment a therapeutically effective amount of a combination of one more CD38 inhibitor selected from the group consisting of daratumumab, isatuximab, CAR-Ts against CD38, GBR 1342, TAK-079, TAK-169, 78c, and apigenin, and immune based therapy to thereby treat the cancer.

2. The method of claim 1, wherein the cancer cells also have KRAS mutation.

3. The method of claim 1, wherein the cancer is a tumor.

4. The method of claim 1, wherein the cancer is lung cancer.

5. The method of claim 1, wherein the immune therapy is small molecule inhibitors, monoclonal antibodies, cancer vaccines, and/or T-cell based therapies.

6. The method of claim 5, wherein the immune based therapy is administration of checkpoint inhibitor.

7. The method of claim 6, wherein the checkpoint inhibitor is directed against immune checkpoints PD-1, PD-L1, LAG-3, Tim-1, 41BB, Ox40 or CD122.

8. The method of claim 1, wherein the one or more inhibitors of the CD38, and immune based therapy are administered at the same or different times, over the same period of time or different periods of time, and by the same route or different routes.

9. The method of claim 6, wherein the one or more inhibitors of the CD38, and the checkpoint inhibitor are administered at a dose of from 1.0 μg/kg to 100 mg/kg.

10. A method for treatment of cancer, wherein the cancer cells are LKB1 deficient, and optionally also have KRAS mutation, consisting of i) administering to an individual in need of treatment, one or more inhibitors of CD38 selected from the group consisting of daratumumab, isatuximab, CAR-Ts against CD38, GBR 1342, TAK-079, TAK-169, 78c, and apigenin; ii) determining that immune checkpoints are upregulated, and iii) administering immune based therapy.

11. The method of claim 10, wherein the administering immune based therapy comprises the administration of a checkpoint inhibitor directed against immune checkpoints PD-1, PD-L1, LAG-3, Tim-1, 41BB, Ox40 and/or CD122.

12. The method of claim 1, wherein the combination consists of the CD38 inhibitor and the immune therapy.

13. The method of claim 12, wherein the CD38 inhibitor is daratumumab.

\* \* \* \* \*

SEQUENCE LISTING

```
<160> NUMBER OF SEQ ID NOS: 2

<210> SEQ ID NO 1
<211> LENGTH: 22637
<212> TYPE: DNA
<213> ORGANISM: Homo sapiens
```

```
<400> SEQUENCE: 1
gcgtgtcggg cgcggaaggg ggaggcggcc cggggcgccc gcgagtgagg cgcggggcgg      60
cgaagggagc gcgggtggcg gcacttgctg ccgcggcctt ggatgggctg ggccccctc      120 gccgctccgc ctcctccaca cgcgcggcgg ccgcggcgag ggggacgcgc cgcccggggc     180
ccggcacctt cgggaacccc ccggcccgga gcctgcggcc tgcgccgcct cggccgccgg     240 gagcccgtg gagcccccgc cgccgcgccg cccgcggac cggacgctga gggcactcgg      300
ggcggggcgc gcgctcgggc agacgtttgc ggggaggggg gcgcctgccg gccccggcg      360 accaccttgg gggtcgcggg ccggctcggg gggcgcccag tgcgggccct cgcgggcgcc     420
gggcagcgac cagccctgag cggagctgtt ggccgcggcg ggaggcctcc cggacgcccc     480
cagccccccg aacgctcgcc cgggccggcg ggagtcggcg ccccccggga ggtccgctcg     540
gtcgtccgcg gcggagcgtt tgctcctggg acaggcggtg ggaccggggc gtcgccggag     600
acgcccccag cgaagttggg ctctccaggt gtggggtcc cggggggtag cgacgtcgcg      660
gacccggcct gtgggatggg cggcccgag aagactgcgc tcggccgtgt tcatacttgt      720
ccgtgggcct gaggtccccg gaggatgacc tagcactgaa aagccccggc cggcctcccc     780
agggtccccg aggacgaagt tgaccctgac cgggccgtct cccagttctg aggcccgggt     840
cccactggaa ctcgcgtctg agccgccgtc ccggacccc ggtgcccgcc ggtccgcaga      900
ccctgcaccg ggcttggact cgcagccggg actgacgtgt agaacaatcg tttctgttgg     960
aagaagggtt tttcccttcc ttttgggtt tttgttgcct tttttttttc ttttttcttt     1020
gtaaaatttt ggagaaggga agtcggaaca caaggaagga ccgctcaccc gcggactcag    1080
ggctggcggc gggactccag gaccctgggt ccagcatgga ggtggtggac ccgcagcagc    1140
tgggcatgtt cacggagggc gagctgatgt cggtgggtat ggacacgttc atccaccgca    1200
tcgactccac cgaggtcatc taccagccgc gccgcaagcg ggccaagctc atcggcaagt    1260
acctgatggg ggacctgctg ggggaaggct cttacggcaa ggtgaaggag gtgctggact    1320
cggagacgct gtgcaggagg gccgtcaaga tcctcaagaa gaagaagttg cgaaggatcc    1380
ccaacgggga ggccaacgtg aagaagtaag tatggcttgc tggggtcggg gccgggccgg    1440
gccagtcacg gtgctgatgg ttctgtcttc cttccttctc tcctccctcc ctcccttact    1500
tcctcttaac accctgagct ggacccgtct ggcgcctgtg tcctccgtgc cagggagagc    1560
gtggttgggg gcctgcgtta cggactttca ctcaggcaag gccagttgtc gcagcggggc    1620
gtgcgtttgc atgggctctt ggactccagt taaaatgccc tggtagcgaa accctcctga    1680
gaagggagcg gccccaatc ccctaagact agccccttgg ctccccagc tgtccaagga     1740 gcagaggcgc ccagtggaat cagcctgtgt ttgtttgggc cccgagagtt tgtgtgcggc    1800
cgccaacacg ttttctgcgc agtgtgtggc cgttaccggg gccaggcgaa atgtgatttg    1860
tttatcctgt cagaggggaa ccctgggctg ccaaaaataa ctgtttgcac cggcttatca    1920
gtcagcagga gggaaacgta gccttttcctc atttgccagg gatgtgacgc tggaagcatc    1980
cctggccccc ggggctggaa gccctgcccg aggggactg tgcctccctc ccgaattgca     2040
tccggaagac cttactttc caactgactt cttcaggcac ggggctgccg ctgggcatcc     2100
cggacgcctc tgcatctgtg cgcggagaag ctcctaccta gggcagcact ggccggcctg    2160
agcctctccc agctggtggg ggtggccggg ggtgtccctg ccttatcgca gccagacacg    2220
ctgcacctgc cgccgcctgg cgggccctgc ccaggccctg ctccttttccc agccttctta    2280 actttcaaaa ctttgcctcc tgtttccaag aaaggacctt atctgctggg ctaggcctcg    2340
```

```
agggactggc aaggacaccc tgcgcagggc accatgacct tggaaggagg tccggggagg    2400
ggctgctgcg gtgtctgctc tcaccttcct cctgctcagg ggccctgggg ctcctgccgt    2460
gtctgctctc acctctctcc tgctcagggg ccctggggct cacgtacatt tttttttttt    2520 ttttttgag acggagtctc gctctgttcc ccaggctgga gtgcagtggc gcgaactggg     2580
ctcactgcaa gctccgcctc ccgggttcat gccattctcc tgcctcagcc tcccgagtag    2640
ctgggactac aggcacccgc caccacgccc ggccaatttt ttgtattttt cagtagagac    2700
ggggtttcac cgtgttagcc aggatggtct caatctcctg acctcgtgat ccgcccgcct    2760
cggcctccca aagtgctggt actacaggcg tgagtcaacg cgtgcggcct tttttttttt    2820
tttttttttt tttttgaga cggagtttca ctcttgttgc tcaggctgga gtgcagtgga    2880
gtggtcttgg ctcactgcaa tctccgcccc ctgggttcaa gtgattctcg tgcctcagcc    2940
tcccgagtag ctgggattac aggtgcctgc cacagtgccc agctaatttt tttttttttt    3000
ttttagtaga cgggggtttt caccatcttg gccaggttgg tcttgaactt ctgacctcgt    3060
gatccacctg cctcagcctc ccaaagtgct gggattaaag gcgtgagcca ccgcgcccgg    3120
ccagcacgct tcttaatcag catgcaggct gtgacatgcg gaaaccaggg gcacaggctc    3180
tgaagtttgt actctggagc tggagcagtc agggttaaat gggagcggct gggaagggtg    3240
tgtttccacg aggcctttct gatgtctcag tgcccagtct ggacccgggt agaaggtgtg    3300
gccagtgcct tgagtcagtg gagcagttgc ctgtgcctgg tctctgtgag atgggttggt    3360
caggggctag gcagagcctg tgcctggtct ctgtgagatg ggttggtcag ggctaggca    3420 gagcctgtgc tgggggtagc aggtgccctc taaaggggcc agtgacagtc tctctcccag    3480
cagtgagaaa cccacgctta ggggccgggc gcggtggctc acgcctgtaa tcccagcact    3540
ttgggaggct gaggtgggtg gatcgcctga ggtcaggagt tcgagaccag cctggccaac    3600
atggtgaaac cccatctcta ctaaaaatac aaaagttagc cgagtgtggt ggcgtgtgcc    3660
tgtaatccca gctactcggg aggctgaggc agaacattgc tggagcctgg gaggcggagc    3720
ttgcggtgac ccgagatcgc accattgcgc tccagcctgg gcgacacagc gagactctgt    3780
ctcaaaaata aataaataaa taaataaata aataaataaa taaataaatc tggcttgagt    3840
tttgacaaat gtatatgcag ggtcaatggg aagacagacg ctggagggtg aagcctgac    3900 tgtgagagtg agcccctgc tttcctgaac agtcagtgga ggaggtcctg ggagctcagg    3960
tgagcacctg aacggtaggg cagagcctga gggtcttggt ggagacaggc aagaaggttg    4020
caggaaccta gtctggccca gtgcctggga aacggagg gaacacgag gcagggaggc     4080 agaggggttg gcaggacctg gactggactg tgcgtcgcag ctacccacag cttgaccca     4140 ctgccttgaa gtgagtgatg caccctcact agtgttcagc gtccaatttc atcctggccc    4200
tgagtgtgta acggctttgc ccttgcgggg cccctgggga tgaggggtga gccctgtccc    4260
ttcctggtca ctgtctgcca tcaggagctg ccccgcttac agctgtgatt caggagccac    4320
tgcatttcct ccagccccct gggtgctgcc aggggtcct cctattctgg gagctggtgt    4380
gttctgactg gaggctgcca tgtgcagagt gctgtcaagg agaagggtg tccactgccc     4440 agccctgagg cccaaggcct tggccagcct tgctgccagc gctgcaggga aaagcctcc     4500 tttgtgtgtg ggaagtttaa taaactccgc tcagattgtg tctcgcagcg agtgtctgga    4560
accttccaga caagcctcag gcgtccggtc ctccagttgg tgtggaaagc gtgggcgatc    4620 accaagggg gtgggttggg gcagatggag ccggcgtgag tcccgtctct tcccttcctt    4680
```

```
cccagaaagg cagccctgga gtccatgcct tgtcccgctc tcaccggcaa aaagtataat      4740
cttattagaa ataggaaagt tccaaaaagc atcaatgagt taaaagagg gctgggcatg       4800 ttcggtcatg cctgtaatcc cagcactttg ggaggccaag gcgggtggat cacccgaggt      4860
tgggagttag cctgaccaac atggtgaaac cctgtctcta ctaaaaatac aaaattagct      4920
gagtgtggtg gcgcacgcct gtaatcccag ctactctgga ggctgaggca ggagaatcac      4980
ttgaacccgg gaagcagagg ttgcggtgag ccaagaccat gccattgcac tccagcctgg      5040
gtaacaagag tgaaactccg tctcgaaaaa aaaagggct ggggccgggc gtggtggctc       5100
acgcctgtaa tcccagcact tgggaggcc gaggcggttt gatcacaagg tcagaagttt       5160
gagaccagcg tggccaacat ggtgaaaccc tctctctact aaaaatagaa aaactagcca      5220
ggtgtggtgg cacatgccaa taatcccagc tacttcatct gaggtcagga gttcaagacc      5280
agcctggcca atatggcgaa actccgtctc tactacaaat acaaaaatta gccaggcgtg      5340
gtggcgcgcg cctgtagtcc agctactggg aagctgaag caaggagaat cgcttgaacc       5400
tgggaggcgg aggttgcggt gagccgagat cgcatcattg cattccaggc tgggcaagcc      5460
taggagagaa gagcgaaatt gtgtctcaaa aaaacaatta attaaaataa atcagtgcc       5520 ataggctgtt tctggtaggc agtgggttcc tagggtggag cagggaaggg ctggaaaggg      5580
tcgcctgtgc ccagcccgac tccccgtgct tctcggggga cagcacggct agctgctgct     5640
gcggagccca cagtggggtt ctgggggggg gggtgcaggc agaaggccgc catgcctccc     5700
tccccctttc caccccagtg agagtgggct cgaaggcagg gagtctgccc gccttgtgga     5760
gcctccgcag aggcacccag ggctgccgtg agcgcacagc ctggcggtgt cccacggccc     5820 tgcccttttcc tgtcacttcc acctgttgca aaacactgtg ctttcgtatc ttttctttct   5880
acctgtttgg aaatgtgaaa atcactgctg ccgtaggaaa cgggcccaga tccgggctgt    5940
ggctctccca tccgcaccgc ccccgcggtg tccagccagg aggtgggagg tgggcggcac    6000
tcagtgtgcc tggttgcggc gatgattggc agatgcttgg acctatggta aagaggattt    6060
tcgcgagctg ggagtcagtc ctggactttg taggtcttta catcccaggc ggcctttatg    6120
gggttccagc atctgctgag gccctgcgc cagccatgtg aggcctgggt gtcctcgagg     6180
cctctgtttg tgcccctctc tgggcagcgg gagggagagc tctgagaccc agagggagct    6240 cagggctgg gcagccgcag aacagcgggg gtaatgggtc cactgggggt tctgggctgt    6300
gcacacagtg ggcttccggt gcccagccag ctggggcagg cctggaatgt tggttcctct   6360
ctcaggatct ggggcgctgc tgtagctgtc ggggaatcag tgaggcggct ggacggcccg    6420
tatatcccac aaacgccacc gtattgctca aactggactc aattttctta acaccttttt    6480 ttttttttt tttttttttt ttggagacag ggtctcactg tatcgccgag gctggagtgc     6540
agtggcgcaa tcatagctct gggctcaggt gaccctcctg cccccaaggt agctgggact    6600
gcagatgtgc accaccacac ccgactagtt ttttgtagag atgggggtttc gccatgttgt   6660 ccaggctggt ctcaaactcc tagactcaag ctatccgcct gcctgggcct cccagagtgc    6720
tgggattaca ggtatgagcc actgcttcgc cacgttcacc tttatttact tatttattta    6780 ttttgagac ggagtctcgc tctgtcccc aggctggagt gctgtggcac gatcttggct      6840
cactgcaagc tccgcttcag cctcccaagt aagctggaac tacaggtgcc tgccaccaag    6900
cctggctaat tttgttttg tatttttagt agagacgggg tttcaccgtg ttagccagta     6960
tggtctcgat ctcctgacct tgtgatccgc ccgcctcggc ctcccaaagt cctgggatta    7020
caggcttgag tcactgtgcc cggcccacct tttttatttt tatttttatag agacaagggc   7080
```

```
ttgctgtgtt gcccaggctg gtcttgaacc cctgacctta agtaatcctc tctggcctcc    7140
caaagtgctg ggattacagg tgtaagccat agtactgggc ctaaagttca ccttttttt    7200 tttttttttt tttttttgaga tggagtctcg ctctgtcacc caggctggag tgcagtggcg    7260
tgatcttggc tcactgcaag ctctgcctcc cgggttcaca ccattctcct gcctcagcct    7320
cccgaatagc tgggactaca ggcgcctgcc accatgcccg ctaatttttt ttgtattttt    7380
agtagagatg gggtttcact gtgttagcca ggatggtctc gatctcctga cctcgtgatc    7440
tgcctgcctc ggcctcccaa agtgctggg ttacaggtgt gagccaccgc acccggcaaa    7500
gttcaccttt ttaaagtgtg taattcagtg gcatatagta cattgacaga gttgcacaac    7560
tatcacctct atcagcttcc agaacattct tgttacccca gaaggaaacc ccgtctctgt    7620
cagccatcac tccccattcc ctccccagtc ccggcaccca cgcattccct tcctgcctct    7680
ggattggcct gtcctgaaca tttcacacga gtggtgtcac acaccgcgtg gccttttgcg    7740
tccggcttgt ctcacggagt gtgctgtcct caaggggcat ccgcgccgtg gcctgggtcc    7800
gaacctctct gctgttcacg gctgcgtcac tttccagtgt gtggagggcc acgctgcgtt    7860
tgactgctca tctgtggctg gacacttggg ctgctcccgc ctctgcctgt gaattgtggc    7920
tgctttggtg cacgtgtgct cagccggcgt ccctctagaa tccttgaggg ccttgtttca    7980
gccacatcag gagggattca ggaccaggg cacgcgggtc tggagctggg tgttcctggg    8040
tctccatgtg cctcccagtc ctgctctgag ccgtgggagg ccggggcgag ggccaggccc    8100
atctcttccc tgtatgatct gtttctaggc agacggaggc tcctagcccc acctctctgt    8160
gagcttgagt ggcgtttatg actctccttc ctatttcctg tcctgctaat caacaagtca    8220
gctaaacagt ccatgctgcc tgggcaagcc cagtaggccc ctaacgtggc acctcggagc    8280
ggctggcgat gccccaagag ccgggcttcc ccctcctgga ggctcttcct gttcctcgcc    8340
aagctcttag gtttcgctgg gcctcctctt ctgctctttt tctggctgga gacgtcagag    8400
gaagcctggc gatctagaga agctgatgtg cacccatcat cccggaggtg actgccacca    8460
ggcgggggtg gctccacccc cactcctccc ctggcataaa tcggggggacg cacgtgcctg    8520 cgcagaatgc cttggtccct tttaattaaa cagacaaccc agtgtccctt ggtctatgct    8580
gacctgctca ggagtgcctg ggctcttcca cgtttcagct gctgtgtgtc ctgctgctgt    8640
gaagtgtccc cgttgaggtg gaggcagggc agggcgcctt cggtgagggc gagtcctcct    8700
gtgcccgttt ccccatctgt agaatgatgg ctcatggagg agacatggtg tcggcaggtg    8760
gtggccggcg cagggaggtt tccaggaggg agtcctccac cctcatttgc ttttagggcc    8820
gtgcagcctc ccgagcggcc cccacgaggc tctgaggctg catgcaggtt gagctcctgg    8880
cctcactgcc cctcctcagg gttaggactg tgctggagcc tgggtgggtg tggggtggtc    8940
cctgcacagg cagcaggagg tgggccagag cggtgctgga cctgaaggcc cgtggctccc    9000
tcagctccac tgaggaggct ggaatagtgt cctgggccac cttccctgcc ggtagccggc    9060
tcctgctgag ggagggggtg ctttcgcctc ctggtggagc atcaggctct tggggcctgt    9120
gcgtccgagc atctggcctc tgctgtctga aaacagcacc ttcccccgcc cccggccacc    9180
gcatctcctc tgaatagaag gcaagtcttg cctcccagga atggcctgtg accttcatca    9240
gcgggggagg ttaggggcac acagagccct ggggaacaag gggatctggg gctgagccgg    9300
gcctctcggg cccaccccga gctctcctga gcagcctggc aggcaggaag gcgctgggcc    9360
ccggggcctt tgccgagccc agcctcaccc tcagcgtccc cctcaatgcc ctgggtgcct    9420
```

```
gccaggctgt ggacacaggc cctggccagt tctataaata accttgccgg gccctgctgg    9480
gaattggtgc caccaccaca tagcccagag agaacggaaa cacagggctt ctcagcgagc    9540
agaccaggcc tgcggtgacc agtggaagtg ggggacgctt tcagggctgg gcagcccgac    9600
agggcaccgg gcacagccag gggcggaac cagttgctca ctggctccgc ttctggggga    9660
ctgtgtccct ctgtgccccg tccccatcac accttgcttt ccctcatcc tgctctccta     9720
gcccctcccc agactggcgg cccccttgtcc aggcccagcc ccagcacagc ctgcagccct   9780
ggcagagctc aggccttggc cttctgaggt tgccctgagg gcagtgagca atgagccctg    9840
ggactggtgc actgggaggg aaaggtgagc caaggcttcc tgcaagaggc agccctgagc   9900
tgggggtggg gaaggctggg tcgtgggata cccctgacac cccaagttttt tttttttgaga 9960
tggagtcttg ctctgtcacc caggctggag tgcagtggtg agatctcgac tctctgcaac   10020
ctccgcctcc caggttcaag cgattctcct gcctcagcct cctgagtagc tgggattaca   10080
ggcgcccatc accacgcccg gctaattttt gtattttag tagagacaag gtttcaccat    10140
gttggccagg ctggttctga actcctgacc tcaggtgatc cacctcggcc tcccatagtg   10200
tcgggattac aggcgtgagt caccgcgcct ggcccccag ctgtttttta tgctccatgc    10260
ttgggcttcc tgttaagaat taaaaagaa aaaaaaact atggagatgg aatttacata    10320
ctgtacaact cattcgttca cagtgtacaa ttcagtggca ttaagtacat tcacacggct    10380
gtgcaaccac tacttctaat tccagaacgt tcggtcaccc caaaagcaag ccccattccc   10440
attgtgtcac tctccatccc ctccaccagc tcctggccac tctgaatcca cttcctggct   10500
ctggattggc ttgtcctgga tattgcatag aaatgggatc ctgtcggccg ggcgcggtga   10560
ctcacgagag caagagatcc agaccatcct ggccaacatg gtgaaacccc atctctacta   10620
aaaatacaaa aattagctgg gcgtggttgc gggcacctgt agtcccagcg actcaggggc   10680
tgagtcagga gaaatcgctt gaacccggga ggcagaggtt gcagtgagct gagatcatgc   10740
cattgcactc tggcctggcg acagagtgag actccgtctc caaaaaaaaa aaaacaagaa   10800
atgggatcct gtcatcccag cgttttccga ggccgaggtg ggcagatgac ttgagcctag   10860
tagttcaaac gagaccagcc tgggcagcac ggtgaaactg tctctactaa aatacaaaaa   10920
ttagctgggc atggtagcac acgtctgtag tcccagctac ttgcggggct gagatgggag   10980
gatcgcttga gcctgggagg tgcactccag cctgggcgac agggaaaccc tgtctcaaaa   11040
aaaaaaaaaa aagtgcatca cacactgtgt gtcctttagt gtctcactgt gacatcctca   11100
aggtgcagct aggctgtggc tcgagtcaga gcctcactgg ttttttgtggc tgagtcttgt   11160
tgagtgcgtg gatgggctgt gctgatcctc gtctgtggaa gggcccctgg gtggttccac   11220
atctcggctg ctgtgcgtcc tgctgctgtg agcatctcgt gctccgtttc tgcgtggcgt   11280
gtactgttcc tcagggtgtg tacctgggag tggagctgct ggctcacagg gtaacagacc   11340
tttggagaag ctgcagacgc ttccacgccc acccactggg tgtgaggacc ttgctcctcg   11400
tcattttttgt ttttgtttaa tttttctctt tatgagacag ggtcttattc tgttgtccag  11460
gctggagtgc agtagcacga tcacaggtaa ctacaggctc aagtgatcct cccacctgag   11520
cctcccgagt agctaggact tgaggcacgt acctccacac ctggctaatt tttgtatttt   11580
tagtagagac agggtttcgc cgtgttgctc aggctggtct cgaactcctg agctcaggtg   11640
atccacccgc ctcggcctcc tatagtgctg ggagaaatga agtgtctgcg acagggcggc   11700
agctgcagag ggggctgtgc tctctggcct gttgtgcccc acccttgtga caggcaggtg   11760
ggcgtggcca actgggcggc agctgcagag ggggcagtga caggcgggtg ggtgtggcag   11820
```

```
gaccccacaa tgtctctttc tgtggcgtct ccttcttcgc ctgcccct tc ctatgggcca    11880 tccttccagc tcacctgcgg cccaccctcc aaggagtggg accctcggag ttgggagccc    11940
ttggctgcgt gggactgtac tgtgtgacgg agccatcacc agggctccaa ctcaccctgg    12000
ctcctgccac agtctgggct ccatctgtgc taccattgca gtagtctggt ttctaggaag    12060
caaaactgtt actgagttac aaagctcaat taagagtgtc ctttgggagg ccgaggcggg    12120
cggatcacaa ggtcaggaga tcgagaccat cctggccaac atggtgaaac cctgtctgta    12180
ctaaaataca aaaaaattag ccggctgtgg tgacacgtgc ctgtagtccc agctactcgg    12240
gaggctgagg cagggaaatc acttgaacct ggggaggcaga ggttgcagtg agctgagatc    12300
gggccaccgt gctccagcct agggacagag caagactctg tctcagaaaa aaaaaaagt    12360 gtcctaactg tgtcctccaa agccctcgcc ggccgatgac agactagagg cgcctgtgct    12420 cccacccct accgccctga gcctggacgc gtggcccctg cagggccctt tcccacagca    12480
ctgtgaactc acagcttctc tctagggaag ggaggaggta cgccacttcc acagggagat    12540
ggggaggccg actccaggga tccaggccat catcctgacg ttgggtcggc tgatacaccc    12600
ctgtcctctc tgtcccaggg aaattcaact actgaggagg ttacggcaca aaaatgtcat    12660
ccagctggtg gatgtgttat acaacgaaga gaagcagaaa atatatcctt tccggtgttg    12720
ggaccgcggg gcctccgtgg gaggggctgg ggccctgggt ccgcctgcct cgaggcctgc    12780
tcctcttccc gtctccttga aggagactgg cacacgaggg ccgtggcctt ccctggttcc    12840
ccggaagtca gccattgtgg caatggctgc gcagcttgct gaaagggggcc ctgagccctg    12900 gcccctgtgt cttgggcccg tggggtgtca agtccctttt ttctcagagt ctcctcccag    12960
gctaaccagg ggtgtagcca cggtctgcct gagacaggcc acgcgggctg accgttgtgg    13020
gccattttgg tcgtggctgg gcgtgtcctc gtgtcatctg tggacacccc catgggtctt    13080
acgggcacag cctccctacg gggactttgc ttcctaaggc cctgtgccca gagcaagagc    13140
cagaagtggt cctgaggctg gggctgtgtt ccctgagcca cgcggtcagg ggccctggga    13200
ccgtcctgca tgggcccgag cctgcttggg ggggcgtcca ggaggcacca tcccccgccc    13260
atgggcaggg tgggggacgt gagccccgca ggaacgctgc cccaagagtc agccctgtcc    13320
tccccttccc cgtaggctcc ttcctcctgg gacgctgggg ccctgggcc ttttcagagg    13380 ggtggctgag gcagggtgg gccctggtcc cgaggagggg caaggtgggt gcagagggtc    13440
cctccagagc cccttttctg gccccgtgc tccctgggcc tgtgagtggg gccgcccct    13500 gagctgtgtg tccttagcgc cccacgtata tggtgatgga gtactgcgtg tgtggcatgc    13560
aggaaatgct ggacagcgtg ccggagaagc gtttcccagt gtgccaggcc cacgggtgcg    13620
tgcgcggggc aggggccagg gtggggcggg ggccggggc caggcagggc aggctccttt    13680
ccgtgaggcc acactgcttg tcctgatatt cattgacatg aaggcccaag ttttttttgtt    13740 tttttgttt tttgtgtttt ttttcgagat ggagtctcac tctgtcgccc aggctggagt    13800
gcaatggtgc gatctcggct cactgcaagc tccgcctccg aggttcacgc cattcttctg    13860
cctcagcttc ccgagtagct gggattacag gcgcccgcca ccacgcccgg ctaatttttt    13920 gtattttag tagagacggg gtttcaccgt gttagccagg atggtctcaa actcctgacc    13980
tcgtgatccg cctgcctcag cctcccaaag tgctgggatt acaggcatga gctaccacgc    14040
ccggccttgt aaaggcccaa gttttttaaaa acagttttgg ggtcccccat gtgtggcatc    14100
cacaggcagg gctgctgcca acctcccgcc tccatctttg ctgggcctgc tgcctgaggc    14160
```

```
cagtggcctg cttccagccc atcgctggca gccgcctgcc ctgaccagat ctcctggatg   14220
caggtctgtg gcctcagagt cagggcccct tgctgctgca ggaccacagg ggcagggagg   14280
ggcctgctgt tccagcaaga ctttggggtg cagccggcct gtggcccaca ggaaaatgag   14340
acctgtggac atccggggcc ctgccagacg tggctcggcc ggacgagggt ggccactgca   14400
ggcgcaggtg tggctccctg ctggacctag ccttcctct gtcctgtgtg cctggacttc   14460
tgtgacttcc cagctgggcc tgtggtgttt gggaggctcc caggcagctg caaaggggac   14520
ccctgtgagg ggcagggagg cctcggcccc aggacgggtg tgtgctgccc gcaggtactt   14580
ctgtcagctg attgacggcc tggagtacct gcatagccag gcattgtgc acaaggacat   14640 caagccgggg aacctgctgc tcaccaccgg tggcaccctc aaaatctccg acctgggcgt   14700
ggccgaggta ggcacgtgct agggggggcc ctggggcgcc ccctcccggg cactccctga   14760
gggctgcacg gcaccgccac aggcactgca cccgttcgcg gcggacgaca cctgccggac   14820
cagccagggc tccccggctt tccagccgcc cgagattgcc aacggcctgg acaccttctc   14880
cggcttcaag gtggacatct ggtcggctgg ggtcaccctg taagtgcccc gccccccgg    14940 gcactcacca cacgcacact ccgaggggcc tctgcgtctt gggcagctgc cggcctgtgg   15000
gcgcagggcg tggccaccgg cccagaccct ctctggccac agccgctagg gggtgcttac   15060
tttatggaaa tgtaactcat acggcagatg gtggttcacc cgtgtgaagt gcagcctggc   15120
ccgtcaggga tcttcacaga gtggcacggc cgaccctcct cccagagccc cacagggaag   15180
ctgggcgggt gacagcagct ccaggccccct tccccgggtg ggtccagagg acactcccct   15240 cctacccgt agcctccact agtggaaggt ggtgaagaca gaggtgtcct tgagtccaca   15300
gggcctctgg tccagcagcc acgggacgcc tctgtccctg gggtagagct ggggctccta   15360
gggcgtcaac caccttgact gaccacgcct ttcttccctc ccctcgaaat gaagctacaa   15420
catcaccacg ggtctgtacc ccttcgaagg ggacaacatc tacaagttgt ttgagaacat   15480
cgggaagggg agctacgcca tcccgggcga ctgtggcccc ccgctctctg acctgctgaa   15540
aggtgggagc ctcatccctc tgcccgcagc ccagggagg cggggctttt gtgcagaaat   15600
gtagggttgg gggtgtcagg tgggggggcta ttggccccga cccccagca ggcattgaga   15660 ggactgagtg gagaggccga cctccccgca gggcctggtt tgccaggtcc ctcagctcca   15720
ccctgcttct gggcccctgtt caccctccga actcccaccc cagagggcag tgctgccctg   15780
cgcctccccc agccccaccc tcgggggctc cctggcttgc agggtctgtc agggttgtcc   15840
tgctgcactt cctacgcatg gcagcaggtg gcactggccg tccgtccatc tgcccagtgg   15900
ccttgggaga acggaaccgc cctggccgtc cagcccagcc ctgtctccct gccagccgcg   15960
cacaggctgt ccccggcatg tcccaggagt ggagtggcct ctgtcaggga gaccgcctgt   16020
gcgcggggtc ccccttagga gcgtccaggt atcacccagg gcctgacaac agaggctggg   16080
caggcgggga cggttggtgg ggtctcaggc ctgtgcccag ctgacaggct cctcgccggc   16140
ttctcctcag ggatgcttga gtacgaaccg gccaagaggt tctccatccg gcagatccgg   16200
cagcacaggt gagcggcccc tgggggcagt ggggccgagg ctgcagggag gccggccatg   16260
tgggcagctg gttgagcggg cgctagcagca gggcgtggtg ggggtgccag gctgggctgg   16320
ggccagaccc cgtgcagcgc ccgcagttct cggggcccga gtgggtctc tgggcagtgt    16380 cctgttaccg gccagaccca ggcgccttgt ccgaactggg gtctgagtga ggacatgcgt   16440
ccgtccctgc cctaggcatg gagatgcgcc aggaagggca cagctggtcc caaacactgg   16500
cgagagcctc tcttttttccc ctcctcctgg ggctcccagc agcagggtgt ggctgggatc   16560
```

```
cagcccaggg cccccagctc catgacaggg aagacagagc agcggacggg gtcagcaggc   16620
cccacagtgc cgcctccctc acttcgtggg ctctgctcct ctgcaccagc cctggaggc    16680 ccttgagccg tctgctggag cccctccgag cccgaggcc acccactgag accggctctg    16740
ggagtgggag tgtccggacc cctgaggcgc tggtgctgat tgtgccttgg gggtctctgc   16800
acagctcggg tcatctgggc gcctggcggg gactggggct gcccccgat agcctcctgg    16860 gctgggatgt gctcagggcc ccccagaccc ccttctggcc tttgctggct ttgcagccag   16920
catccatctg gtgggtgctg gcttctgagt gccacctggg acacaggcct cagggtggag   16980
gggacatctg tcaggcttgg agtcaggtca gcctgcctgc tcctagagga catggctgag   17040
cttctgtggt cacagccacc ccttgcacgg cctggtccca gctcctgagt gtgtggcagg   17100
taccctgggc ccagaggagc tgggtcggaa aactggaccg ccctggtgcc agcctgacag   17160
gcgccactgc ttctgggcgt ttgcagctgg ttccggaaga aacatcctcc ggctgaagca   17220
ccagtgccca tcccaccgag cccagacacc aaggaccggt ggcgcagcat gactgtggtg   17280
ccgtacttgg aggacctgca cggcgcggac gaggacgagg acctcttcga catcgaggat   17340
gacatcatct acactcagga cttcacggtg cccggtgagt ctggcggggg ccctgcccg    17400 gctctgctga ctcggccagg atgtcccacg ggagcagggt gcctgcctgt ctgcaacaag   17460
gacagcttct gccctctggt ggccaatccc acgtccccaa agcctccagc ccacctgcag   17520
gctgcctccg ccctgcgggc cgctgggaca tggctgaaag gtgtggggtc agcggggca   17580 ccagcccagg cctgtctggc caggagggtt cctcaggcgt ctctccgggt gctgcccagc   17640
caggcaccac ccaccggcct tggcctgagt cccagcagga gcaggcgggg gagccccagg   17700
gtcgggggag ggtaggtgag agtcagggtg cagggtggcc cctcagacag ctggcatgag   17760
agagggtcca gtggccctcc ctcccgtcgt ccctgaggcc tgcccgctgg ccctgatgcc   17820
ggccgccctt cttccctagg tggcgaggag gcgtctgagg cagggcttag agcggagcgc   17880
ggcttgcaga agagcgaggg ctcagacctt tcaggagagg aagcctctcg gccggcgccg   17940
cagtagtgcc tgaggaggag ctcagggcct tagcgtaggg gcggcccaca ttggcagcca   18000 gccccctcccc gccatgctcc cggcttggct gtgttcggcc cagggctggg ccgtgtcata   18060 aagagtttg cagtgtatct gcagggtgga tgcttgctgc gctcgggctg gagcctgagg    18120
gggctttctg ctttactgtt tcagcgggaa gtggtgggca ggggccggcc tgagaagggg   18180
ggtacgccag gcaggttggg atgtgaggac ccagtgcaca gggtccaccc ccgggcccga   18240
gggtcccaga atagtggggg ccctgcagag agcccccat taggtccctc agcactcctg    18300 ggccctcat caaaccccta ggctcagctc agtagctggt ccccaggaga gtacagtgtg    18360
ggggcccccg agagcacagt gtatgggggt cccgggggg tacagtgtct gggggccccc    18420
caggaggatg cagcatgtgg gggcccccca ggagggtaca gcgtgtgtgg ggccccagg    18480 atcacaggt ctcagctcct gggctcttgg atttgcagca ccacgaccat cgcgtctggt    18540
ctgttggaac gggaggtgct gctgggtacc ctggtcacta gggtgtgctg ggaggtgggg   18600
gcccctcatg gtgcccatcc ttggggcctg gctgcaattt gacccagcc ccagggtctt    18660 ctgcctttca gagccctggt gcctgagac gggcagccag gcaaatccca ggcaggaggg    18720
ccagttaggg cagggccagc ccaggcaggt tgcgagagtc cctactggga cgtggaccac   18780
acgctgaccc ccacggccgc ccctgcaggc caggatccct gagccaggac ccggcactgg   18840
cttccctcct ggggacccctc aggcctgtgt gagacctggg ctgccctggg gtgaggtgcc   18900
```

```
tgggaggaga gcaggggctg ggccaccttt tcatgaccc tgctaagccc actgtgggtg      18960
gtgaggagga gtacccagca gggggaaggg ccgccagacc actcggcatg gctgaggcct      19020
cagtactcag tactgggtac tcaggtggac gcccctccca ctgctcagat gctggggaca      19080
ggctcaactt caggcttcag cgtgagcccg gtccctgacc tgcagagccc ccttgcgttg      19140
gggcaggaca gcccggcgcc ctcgggtcag gccatcctct gcgctctgcc ggggctgctg      19200
catcggcctc tgcgtgcctc cactttggcc tcacgtgtcc ctacccagga tgcgggtcct      19260
gctgccaaca cccagatccc agggaagggg cttgggctag atcctgggca ccagtgcaga      19320
caggagtgtg gggtggggca agggcccagt ggcggctgtg cccgctgatg cagagctggg      19380
gcaccttgtc cacagggtct gccccaccag agacgggctg ggcccaagct cagacctatg      19440
ggtgcaattg gtgcctcctc accaaggtct tttttatctt tttttttttt tggagacaga      19500
gtcttgctct gtcgcccagg ctggagtgct gtggtgcgat ctcggctcac tgcaacctcc      19560
acctcccgga ttcaagcaat tctgcctcag cctcctgagt agctgggatt acaagtgcgc      19620
gccagcatgc ccggctaatt tttgtatgtt tagtagagac ggggggttca ccatgttggt      19680
caggctggtc tcaaactcct aacctcatga tctgcccacc tcggcctccc aaagtgctgg      19740
gattacaagc gtgagccacc gcgaccggcc caaggtgctt ttttaaagct agtgacttcc      19800
tgtgcacatg gggtgggtgt gtggcaagtt ctggaagctg ctgagtcagc cactggtcca      19860
ttctcggagc tggggctctg cactgggcac atgagctctg gggcagcccg gggcggcctc      19920
ccactgactt cgcccgggag gggcctcggg gatggctcgg cagccagtgt gttcgcggag      19980
tcctcgccaa ccaccacggc tcctcgcagg gacagtacgt gggcagcttc ctgcactttc      20040
ccctgccatt gtgagaacag tgtccacctg gcagggtgg gcagccccag gcctgtgggt       20100
ttcaccaggg tgctggtgat ggttggtggc tagcagggac tgggggcagc tgggggccct      20160
ggcaggctga gctctgctcc ccgcgtggtt ctgtgctggc atttcgcgtg cctggcctga      20220
gcctggcccg agcctggccc tcctgtgtcc tcacagatga gcatgtggcg gctcctgggc      20280
ctctagaacc aaccatgggc cagggtgccc caggggagca cgggagggtc ctgccttgtc      20340
agcttgcctc ctactcgtga ggttcctgca gtcagtacct gggtggggtc ccacctgcgg      20400
ccatggcagg tgcaacagac gtggtggagg ggacactcct gcccaggcca tctgcgggag      20460
gctcagcccc gggggtgcc tcccagagct gctggggggc agcatttcag gctggataca       20520
cctgggcctg acccggggc gggcatggcc tgggcagcag ctgtaagtgc gtccccgtgg       20580
tgggggccag ccaggtccct gtggctctgg ggttgcgccc tcagctcag gccacacttg       20640 ccgtctccct cccaggacag gtcccagaag aggaggccag tcacaatgga cagcgccggg      20700
gcctccccaa ggccgtgtgt atgaacggca cagaggcggc gcagctgagc accaaatcca      20760
gggcggaggg ccgggccccc aaccctgccc gcaaggcctg ctccgccagc agcaagatcc      20820
gccggctgtc ggcctgcaag cagcagtgag gctggccgcc tgcaggtggg gcgcggcggg      20880
gcccgggtgg ggcatgtggg gacaacgcct ggatgccaca gccagccgtg agcatagccc      20940
gcgctagtca gtcatggtga ccgtcacgtg gctgcgcgtg gttgccatgt ggcctttggg      21000
tggcttggcc acgtagcgat ccccgtggag ggtgccgtct cggggcctgg tgtctggcca      21060
gcgtgctggt catggaggcc tacgtgtggc ggggctctgg ggggcgtgc cgtcctcaca       21120 gccacctctc agagtgggtg cattccgagg accctgccct gggcctggcg ccccctcccc      21180
atgcccgcgc gcttccagg aaaggcttat gctgggctca gcccagaggc ttttgagcac       21240
cagtgggtgg tgggtggtgg ggaggggccg cggcctccat ggctctgccg gggtgccgca      21300
```

```
ggctctgagc cagctgccaa gtatggctga ggctgagtcg tgccggacgc tgccctgtct   21360
ctccctgtgt gcctgcctcc tctcccagcc ccagccccag cccgggtgg gagacggagt    21420
cccagaggtg tcagagaccc ttaagtcacc tgccgaggat gcggggtgga tgggggcccg   21480
aggctgaagc cctgccttg ccacagcccc tctcccaggt tttgggggcc accgcctgag    21540
ttacatgtct gtcccccaaa tgggtgccca gcccatcc accagcgtca gagcccgcca     21600
ggccccactg caaaaggcca cacaatgtac cccgggagtg actcaagggt ggccttccct   21660
ggcctcccct gctgcccccc aggagtccgg tagccccatg actgtacctc agcttctcca   21720
tcctcccagg ggcccgcggg aggcggagaa ccggtgccca ggctgacctc ttccgtcttc   21780
cttccaccct gcagcccgtg tccaggagcc ccgccaggtg cccgcgccag ccctcagtc    21840
ttcctgccgg ttccgcccgc cctcccggag aggtggccgc catgcttctg tgccgaccac   21900
gccccaggac ctccggagcg ccctgcaggg ccgggcaggg ggacagcagg gaccgggcgc   21960
agccctcccc cctcggccgc ccggcagtgc acgcggcttg ttgacttcgc agccccgggc   22020
ggagccttcc cgggcgggcg tgggaggagg gaggcggcct ccatgcactt tatgtggaga   22080
ctactggccc cgcccgtggc ctcgtgctcc gcagggcgcc cagcgccgtc cggcggcccc   22140
gccgcagacc agctggcggg tgtggagacc aggctcctga ccccgccatg catgcagcgc   22200
cacctggaag ccgcgcggcc gctttggttt tttgtttggt tggttccatt ttctttttt    22260
ctttttttt ttaagaaaaa ataaaaggtg gatttgagct gtggctgtga ggggtgtttg    22320
ggagctgctg ggtggcaggg gggctgtggg gtcgggctca cgtcgcggcc gcctttgcgc   22380
tctcgggtca ccctgctttg gcggcccggc cggagggcag gaccctcacc tctcccccaa   22440
ggccactgcg ctcttgggac cccagagaaa acccggagca agcaggagtg tgcggtcaat   22500
atttatatca tccagaaaag aaaaacacga gaaacgccat cgcgggatgg tgcagacgcg   22560
gcggggactc ggagggtgcc gtgcgggcga ggccgcccaa atttggcaat aaataaagct   22620
tgggaagctt ggacctg                                                  22637
```

<210> SEQ ID NO 2
<211> LENGTH: 433
<212> TYPE: PRT
<213> ORGANISM: Homo sapiens

<400> SEQUENCE: 2

```
Met Glu Val Val Asp Pro Gln Gln Leu Gly Met Phe Thr Glu Gly
1               5                   10                  15

Leu Met Ser Val Gly Met Asp Thr Phe Ile His Arg Ile Asp Ser Thr
            20                  25                  30

Glu Val Ile Tyr Gln Pro Arg Arg Lys Arg Ala Lys Leu Ile Gly Lys
        35                  40                  45

Tyr Leu Met Gly Asp Leu Leu Gly Glu Gly Ser Tyr Gly Lys Val Lys
    50                  55                  60

Glu Val Leu Asp Ser Glu Thr Leu Cys Arg Arg Ala Val Lys Ile Leu
65                  70                  75                  80

Lys Lys Lys Lys Leu Arg Arg Ile Pro Asn Gly Glu Ala Asn Val Lys
                85                  90                  95

Lys Glu Ile Gln Leu Leu Arg Arg Leu Arg His Lys Asn Val Ile Gln
            100                 105                 110

Leu Val Asp Val Leu Tyr Asn Glu Glu Lys Gln Lys Met Tyr Met Val
        115                 120                 125
```

```
Met Glu Tyr Cys Val Cys Gly Met Gln Glu Met Leu Asp Ser Val Pro
    130             135             140
Glu Lys Arg Phe Pro Val Cys Gln Ala His Gly Tyr Phe Cys Gln Leu
145             150             155                         160
Ile Asp Gly Leu Glu Tyr Leu His Ser Gln Gly Ile Val His Lys Asp
                165             170                 175
Ile Lys Pro Gly Asn Leu Leu Leu Thr Thr Gly Gly Thr Leu Lys Ile
            180             185                 190
Ser Asp Leu Gly Val Ala Glu Ala Leu His Pro Phe Ala Ala Asp Asp
        195             200             205
Thr Cys Arg Thr Ser Gln Gly Ser Pro Ala Phe Gln Pro Pro Glu Ile
    210             215             220
Ala Asn Gly Leu Asp Thr Phe Ser Gly Phe Lys Val Asp Ile Trp Ser
225             230             235                         240
Ala Gly Val Thr Leu Tyr Asn Ile Thr Thr Gly Leu Tyr Pro Phe Glu
            245             250             255
Gly Asp Asn Ile Tyr Lys Leu Phe Glu Asn Ile Gly Lys Gly Ser Tyr
            260             265             270
Ala Ile Pro Gly Asp Cys Gly Pro Pro Leu Ser Asp Leu Leu Lys Gly
            275             280             285
Met Leu Glu Tyr Glu Pro Ala Lys Arg Phe Ser Ile Arg Gln Ile Arg
    290             295             300
Gln His Ser Trp Phe Arg Lys Lys His Pro Pro Ala Glu Ala Pro Val
305             310             315                         320
Pro Ile Pro Pro Ser Pro Asp Thr Lys Asp Arg Trp Arg Ser Met Thr
            325             330             335
Val Val Pro Tyr Leu Glu Asp Leu His Gly Ala Asp Glu Asp Glu Asp
            340             345             350
Leu Phe Asp Ile Glu Asp Asp Ile Ile Tyr Thr Gln Asp Phe Thr Val
        355             360             365
Pro Gly Gln Val Pro Glu Glu Ala Ser His Asn Gly Gln Arg Arg
    370             375             380
Gly Leu Pro Lys Ala Val Cys Met Asn Gly Thr Glu Ala Ala Gln Leu
385             390             395                         400
Ser Thr Lys Ser Arg Ala Glu Gly Arg Ala Pro Asn Pro Ala Arg Lys
            405             410             415
Ala Cys Ser Ala Ser Ser Lys Ile Arg Arg Leu Ser Ala Cys Lys Gln
            420             425             430
Gln
```